US010238307B2

(12) United States Patent
Schlumpf et al.

(10) Patent No.: US 10,238,307 B2
(45) Date of Patent: Mar. 26, 2019

(54) MULTI-CHANNEL CATHETER CONNECTION FOR ANATOMICAL MANOMETRY

(71) Applicant: Laborie Medical Technologies Canada ULC, Mississauga (CA)

(72) Inventors: Peter Schlumpf, Ellikon an der Thur (CH); Ing Han Goping, Oakville (CA); Matthias Stadler, Mannedorf (CH); Tristan Zimmerman, Guelph (CA); Bryce Smith, Sandy, UT (US)

(73) Assignee: Laborie Medical Technologies Canada ULC, Mississauga (CA)

( * ) Notice: Subject to any disclaimer, the term of this patent is extended or adjusted under 35 U.S.C. 154(b) by 117 days.

(21) Appl. No.: 15/430,967

(22) Filed: Feb. 13, 2017

(65) Prior Publication Data

US 2017/0265762 A1     Sep. 21, 2017

Related U.S. Application Data

(60) Provisional application No. 62/310,496, filed on Mar. 18, 2016, provisional application No. 62/349,461, filed on Jun. 13, 2016.

(51) Int. Cl.
*A61M 29/00* (2006.01)
*A61B 5/03* (2006.01)
(Continued)

(52) U.S. Cl.
CPC ............ *A61B 5/037* (2013.01); *A61B 5/036* (2013.01); *A61B 5/04* (2013.01); *A61B 5/6853* (2013.01);
(Continued)

(58) Field of Classification Search
CPC ...... A61B 2560/0214; A61B 2562/227; A61B 5/01; A61B 5/036; A61B 5/037;
(Continued)

(56) References Cited

U.S. PATENT DOCUMENTS 5,609,060 A  *  3/1997  Dent ..................... A61B 5/037
                                                          73/700
6,447,462 B1     9/2002  Wallace et al.
(Continued)

FOREIGN PATENT DOCUMENTS

EP          360286 A2     3/1990
EP         1255485 B1     1/2008
(Continued)

OTHER PUBLICATIONS

International Patent Application No. PCT/CA2017/050343, International Search Report and Written Opinion dated Jun. 27, 2017.

*Primary Examiner* — Jason Flick
(74) *Attorney, Agent, or Firm* — Fredrikson & Byron, P.A.

(57) ABSTRACT

An anatomical manometry catheter system, comprising a plurality of balloons on the distal end and being configured to be inflatable and/or deflatable. The system includes a connector assembly coaxially aligned with the catheter assembly, the connector assembly being connectable to the proximal end of the catheter. The connector assembly may have a connector interface connected to the proximal end of the catheter. The connector assembly may include a manifold comprising a plurality of channels configured to deliver the pressure transmission medium therethrough toward a respective catheter lumen for inflating one or more balloons. The connector assembly may include a charging mechanism fluidly coupled to the catheter that facilitates inflating each balloon of the plurality of balloons by a common actuating
(Continued)

mechanism so as to simultaneously charge each balloon of the plurality of balloons.

28 Claims, 17 Drawing Sheets

(51) Int. Cl.
*A61B 5/04* (2006.01)
*A61B 5/00* (2006.01)
A61B 5/053 (2006.01)
A61B 5/01 (2006.01)
A61B 5/0402 (2006.01)
A61B 5/0488 (2006.01)
A61B 5/11 (2006.01)
A61B 5/145 (2006.01)

(52) U.S. Cl.
CPC .............. *A61B 5/01* (2013.01); *A61B 5/0402* (2013.01); *A61B 5/0488* (2013.01); *A61B 5/0538* (2013.01); *A61B 5/1107* (2013.01); *A61B 5/14539* (2013.01); *A61B 5/4233* (2013.01); *A61B 2560/0214* (2013.01); *A61B 2562/227* (2013.01)

(58) Field of Classification Search
CPC ....... A61B 5/04; A61B 5/0402; A61B 5/0488; A61B 5/0538; A61B 5/1107; A61B 5/14539; A61B 5/4233; A61B 5/6853
USPC ...................................................... 604/99.01
See application file for complete search history.

(56) References Cited

U.S. PATENT DOCUMENTS

| | | | |
|---|---|---|---|
| 7,947,001 B1 | 5/2011 | Sarvazyan | |
| 8,360,988 B2* | 1/2013 | Bobo, Sr. ............... | A61B 5/031 600/561 |
| 2013/0184612 A1* | 7/2013 | Quackenbush ...... | A61B 5/6847 600/587 |
| 2016/0029912 A1 | 2/2016 | Stimpson | |

FOREIGN PATENT DOCUMENTS

| | | |
|---|---|---|
| EP | 1892010 B1 | 10/2010 |
| EP | 1994387 B1 | 3/2012 |
| FR | 2673524 A1 | 11/1992 |
| GB | 2318513 A | 4/1998 |
| WO | 2013109938 A1 | 7/2013 |

* cited by examiner

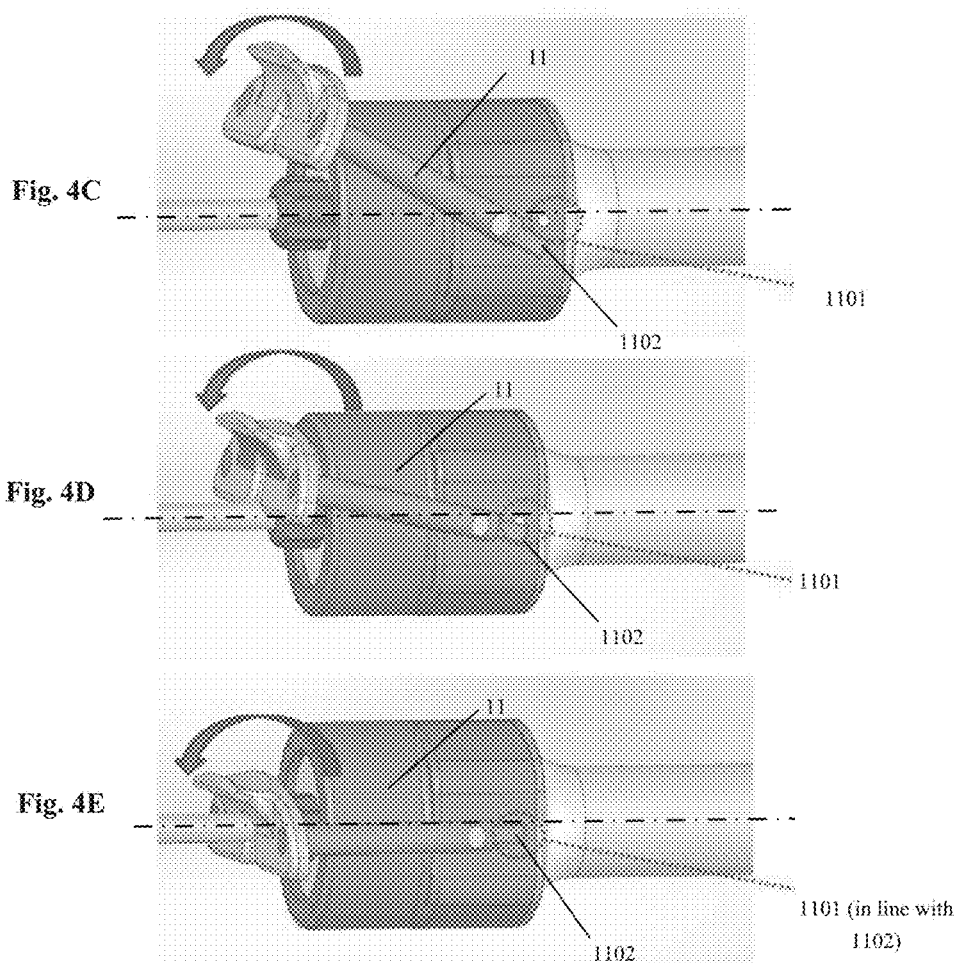
Fig. 4C
Fig. 4D
Fig. 4E
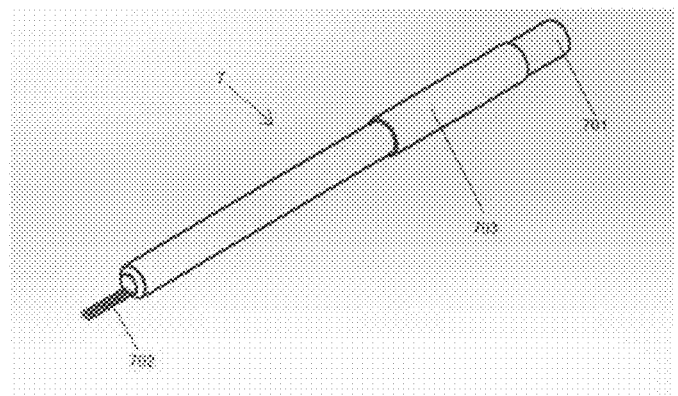
Fig. 5

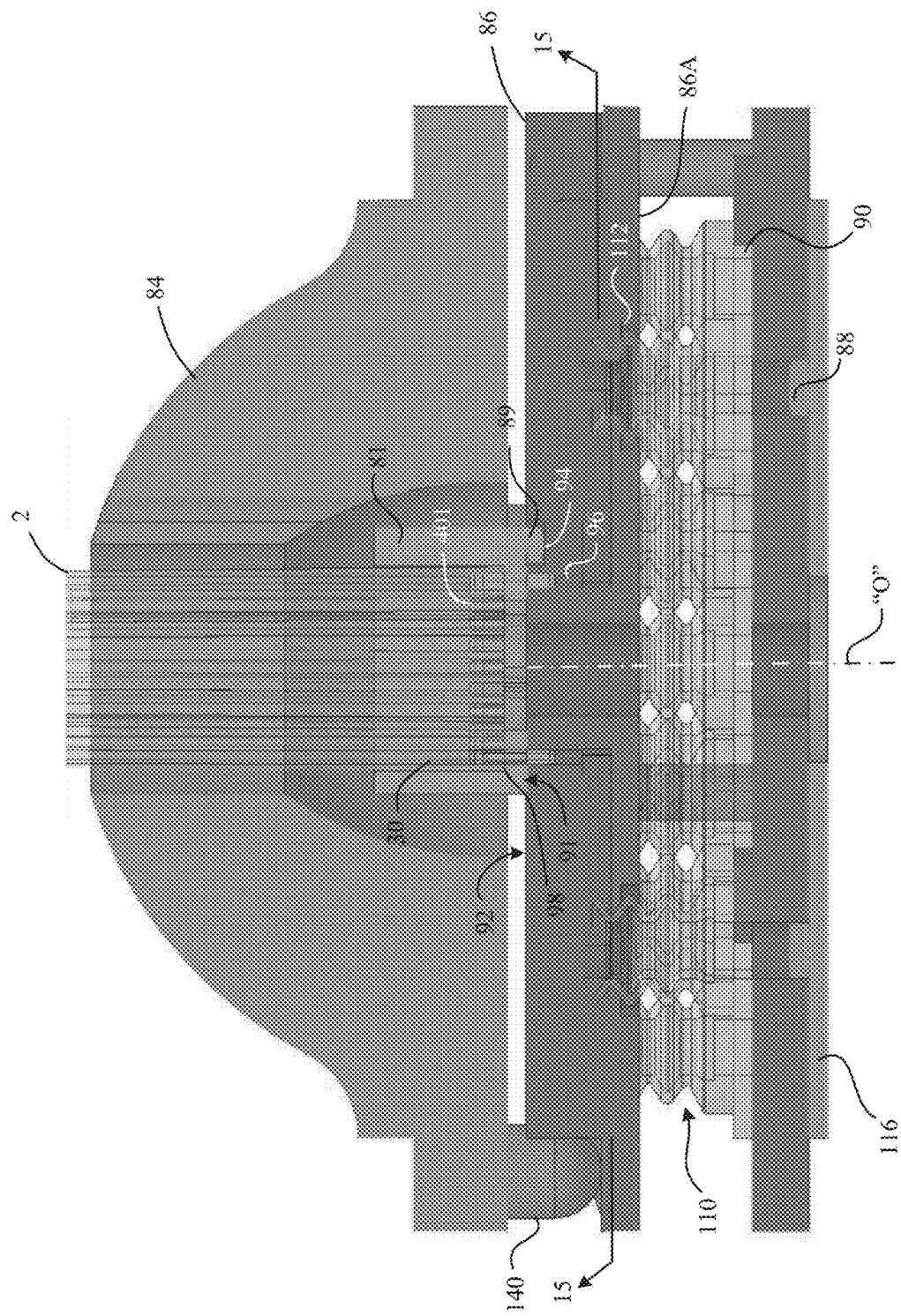

MULTI-CHANNEL CATHETER CONNECTION FOR ANATOMICAL MANOMETRY

RELATED APPLICATIONS

This application claims the benefit of U.S. Provisional Patent Application No. 62/310,496 filed Mar. 18, 2016, and U.S. Provisional Patent Application No. 62/349,461, filed Jun. 13, 2016, the entire contents of each of which are incorporated herein by reference.

BACKGROUND

Today's medical professionals make use of catheters to gain access to interior regions of the body, in order to obtain and document objective measurements of an intended physical parameter. In one example, during anorectal manometry, pressures in the anus and rectum are quantified, giving an indication of any weakness or defect that could be present in the surrounding tissues. Anorectal manometry is a widely performed test for the assessment of anal sphincter function and anorectal co-ordination. Traditionally, manometry has been performed using either solid-state or water-perfused catheters incorporating a limited number of recording channels (typically less than or equal to six recording channels). However, with the development of high-resolution manometry, an increased number of closely spaced micro-transducers can be used to greatly enhance the spatial resolution of such measurements and the ability to measure pressure changes in a circumferential direction. Moreover, such technology has resulted in a paradigm shift in manometric testing of the upper gastrointestinal (GI) tract, with high-resolution manometry now having replaced traditional manometry as the gold-standard investigation of esophageal function. Generally speaking, the more measurement points that can be quantified give the professional more information and a better depiction about the clinical condition of the patient.

Existing devices use of a high number of pressure connection ports and may require the user to connect each port individually, which can be time-consuming and cumbersome.

SUMMARY

In one aspect, this disclosure is directed to an anatomical manometry catheter system, comprising a catheter having a plurality of catheter lumens permitting passage of a pressure transmission medium. The catheter may have a plurality of balloons fluidly coupled to one of the plurality of catheter lumens so as to receive the pressure transmission medium. Each balloon can be inflatable and/or deflatable. The system includes a connector assembly coaxially aligned with the catheter assembly connectable with the catheter. The connector assembly may have a manifold comprising a plurality of channels configured to deliver the pressure transmission medium therethrough toward a respective catheter lumen for inflating one or more balloons. The connector assembly may have a charging mechanism fluidly coupled to the catheter. The charging mechanism may facilitate inflating each balloon of the plurality of balloons by a common actuating mechanism so as to simultaneously charge each balloon of the plurality of balloons.

In another aspect, the connector interface may have an alignment element to permit alignment between the catheter and the connector interface. Further, the charging mechanism may comprise a plurality of bellows fluidly coupled to the channels of the manifold so as to permit passage of the pressure transmission medium from the charging mechanism toward the catheter lumen. The bellows may be commonly actuable when the manifold is connected with the connector interface by a complementary connection so as to simultaneously charge each balloon of the plurality of balloons.

In a further aspect, the manifold can be rotationally connected with the connector interface by a rotationally complementary connection, such that the connector interface is rotatable relative to the manifold. The rotation of the connector interface relative to the manifold may permit an axial displacement of the manifold relative to a bellow housing commonly housing each bellow so as to simultaneously actuate each bellow positioned on the bellow housing, the commonly actuated bellows further permitting simultaneously charging each balloon of the plurality of balloons.

The details of one or more examples are set forth in the accompanying drawings and the description below. Other features, objects, and advantages will be apparent from the description and drawings, and from the claims.

BRIEF DESCRIPTION OF DRAWINGS

FIGS. 4C-4E illustrate perspective view of the charging mechanism of FIG. 4A to show various positions of the handle, with FIGS. 4C and 4D showing the handle in the unlocked position, and FIG. 4E showing the handle in the locked position;

FIG. 5 is a perspective view of a pressure transducer sub-assembly;

FIG. 11 is a sectional front view of the connector assembly of FIG. 10 taken along the plane 10-10;

DETAILED DESCRIPTION

Figure 1A:
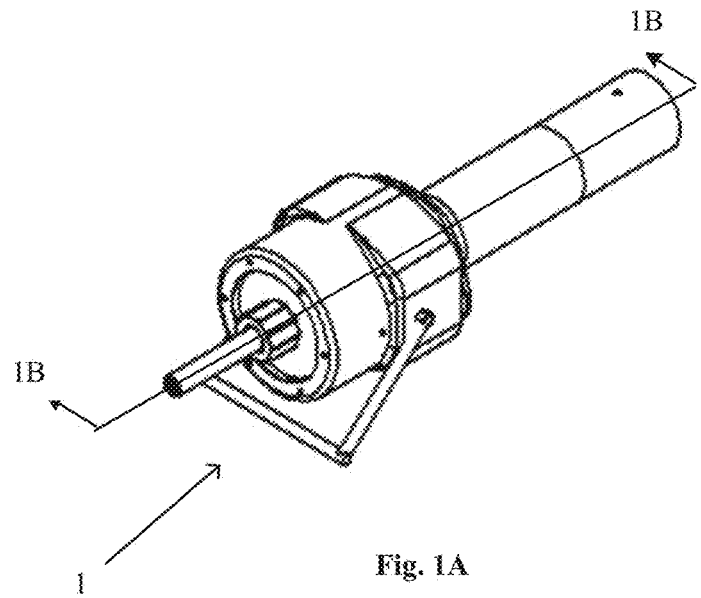
FIG. 1A is a perspective view of a multi-channel catheter connection system used in the air-charged configuration according to an embodiment.
Figure 1B:
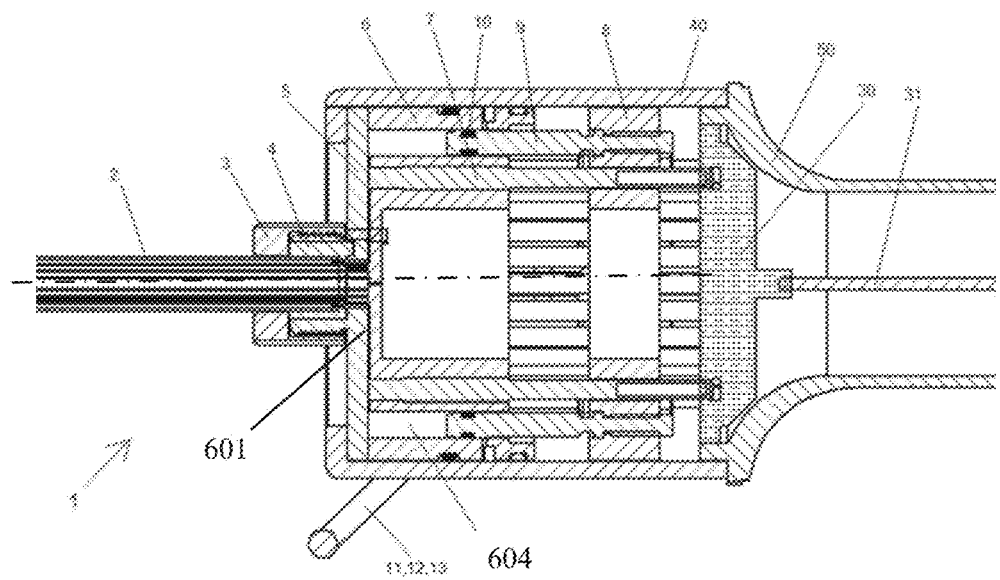
FIG. 1B is a sectional view of the multi-channel catheter connection system of FIG. 1A taken along the sectional plane 1B-1B.

FIGS. 1A-1B illustrate a perspective view and a sectional view taken along 1B-1B respectively of a multi-channel catheter connection system 1 according to an embodiment of the present disclosure. Such a system includes a catheter 2 with a plurality of channels in which a fluid column (e.g., air or water) transmits pressure from a patient's anatomical lumen (e.g., esophagus, anus, rectum, and the like) to a pressure transducer 7 housed at a proximal end 2a of the catheter 2. The embodiments illustrated in FIGS. 1A-1B involve operation of the system 1 in an "air-charged" mode, wherein a sealed air column of known volume inflates a plurality of catheter balloons 40 housed at a distal end 2b within the patient's anatomical lumen. The air column transmits pressure to a pressure transducer 7 located at the proximal end 2a, from which the pressure of the patient lumen can be determined.

Figure 2A:
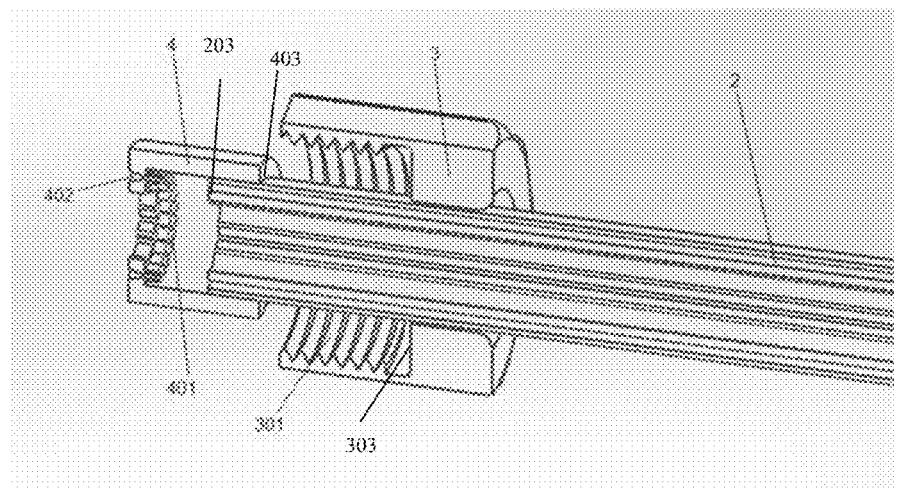
FIG. 2A illustrates a portion of FIG. 1B to show details of a catheter sub-assembly.

The catheter connection system 1 shown in FIGS. 1A-1B comprises a catheter sub-assembly 2, 3, 4, best illustrated in FIG. 2A. The catheter 2 can be generally elongate in shape and be generally hollow to facilitate passage through patient anatomy. The catheter 2 comprises a distal end 2b and a proximal end 2a opposite thereto. In FIG. 2A, the proximal end 2a is near the reference numerals 3-4, while the distal end 2b is not visible. During use, the distal end 2b is placed inside a patient to deliver fluids and/or measure pressure of the patient's anatomical lumen.

Figure 2B:
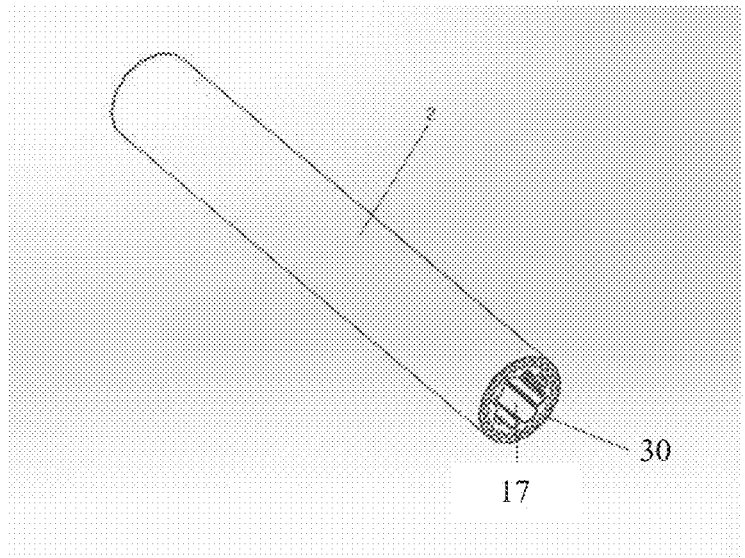
FIG. 2B is a perspective view of a portion of a multi-channel catheter according to an embodiment.
Figure 2C:
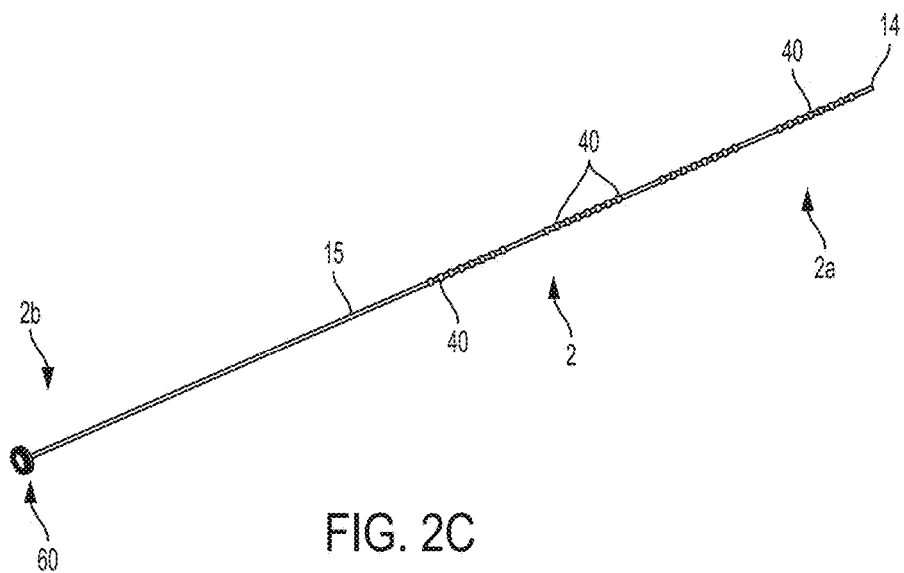
FIG. 2C is another perspective view of the multi-channel catheter shown in FIG. 2B.
Figure 2D:
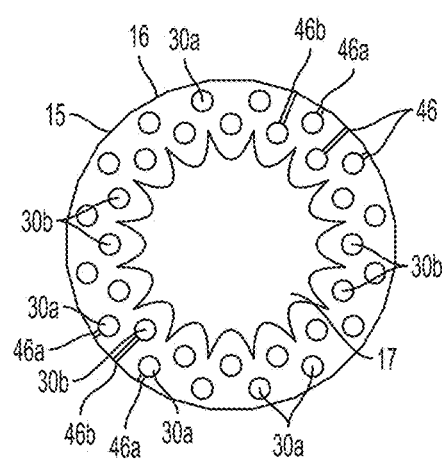
FIG. 2D is a side view of the multi-channel catheter shown in FIG. 2B.
Figure 2E:
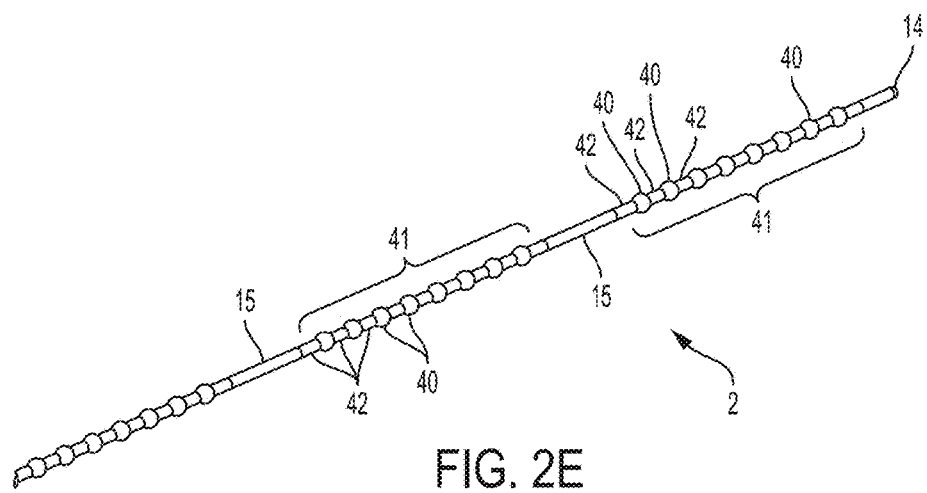
FIG. 2E is a perspective view of the distal portion of the multi-channel catheter shown in FIG. 2B.

With continued reference to FIG. 2A and referring now to FIG. 2B, the catheter sub-assembly 2 comprises a catheter connector 4 and a threaded cap 3, wherein the catheter 2 is coupled to catheter connector 4. The catheter connector 4 comprises multiple slip-on nips 401 and cones 402, for interfacing with pressure lumen 30 of the catheter 2 and corresponding channels on the catheter connector 4 sub-assembly, as will be described further below. The distal end 2b of the catheter 2, in such cases, may comprise one or more catheter balloons 40 that may be charged (e.g., with air). When charged, the catheter balloons 40 may inflate and be at a pressure which opposes (and is equal in magnitude to) the pressure of a lumen in patient's anatomy. Pressure transducers 7 and electrical connections connected to the catheter 2 may permit measurement of the anatomical features of interest. As seen in FIG. 2B, the catheter 2 comprises a plurality of pressure lumen 30 that are disposed about the circumference of a central lumen 17. A pressure transmission medium (e.g., air or water) may pass through the pressure lumen 30, as will be described further below to enable pressure measurement. Optionally, the catheter 2 can also be used to deliver fluids (e.g., water) to the patient when the system 1 is used in a perfusion mode described with respect to FIG. 7A below. In some embodiments, the catheter sub-assembly 2 can be disposable. In such embodiments, indicators can be provided on the catheter 2 to prevent reusing the catheter subassembly. For example, a RFID chip or similar means may be provided for preventing re-use of the catheter sub-assembly 2.

FIGS. 2C-2F illustrate various views of the exemplary catheter 2 suitable for use with an anatomical manometry system according to a non-limiting embodiment. With reference to FIGS. 2C-3F catheter 2 is shown having a plurality of flaccid, thin-walled membranes (e.g., a medical grade balloon 40) each defining an interior expandable and deflatable volume, disposed thereon. The catheter 2 can be used in any of the embodiments illustrated herein. The distal end 2b of the catheter 2 comprises a soft, pliant tip 14, which facilitates insertion of the catheter 2 into the patient. The soft tip 14 may preferably be formed of a material which is pliant enough to deflect or give as the tip 14 encounters a resistive force, such as the wall of the bladder. A low durometer plastic or elastomer, such as polyvinyl chloride (PVC) or a polyurethane, is suitable though other materials having a suitable rigidity/pliancy and are safe for use inside a subject or patient can be used. The tip 14 is formed from an elongated hollow tube 15 which extends from the tip 14 at its distal end 2b to one or more male connectors on its proximal end. The hollow tube 15 is formed of flexible, biocompatible material, such as PVC or a polyolefin, with sufficient properties, such as wall thickness, to resist collapse under normal conditions, and sized in length to extend from within a cavity (e.g., the esophagus) of a patient to outside the mouth or nose of the patient.

In one aspect, the hollow body comprises a central lumen 17. The central lumen 17 extends from a proximal end 2a to a distal end 2b of the catheter 2. One or more secondary lumens 30 (also referred to as "monitor lumens") is disposed within the hollow tube 15, as shown more fully in FIG. 2D. In one aspect, the secondary lumen 30 is hollow and comprises one or more flexible, biocompatible materials, such as polyurethane and is integrally formed from or with the sidewall 16 of the hollow tube 15. The secondary lumens 30 are sized in diameter to fit within the hollow tube 15 and to leave adequate space for passage of fluids through central lumen 17. The secondary lumen 30 may extend over a substantial (e.g., entire) length of the catheter 2.

In accordance with one aspect, a plurality of lumens 30 are disposed between the central lumen 17 and the sidewall 16 of hollow tube 15. A first set of lumens 30a is disposed about the inner circumference of the sidewall 16 nearer the exterior of the sidewall 16. A second set of lumens 30b is disposed about the inner circumference of the sidewall 16 nearer the interior (or central lumen 17) of the sidewall 16. The first set of lumens 30a are offset or spaced from one another so as to provide a section of sidewall 16 between each of the lumens 30. The section of sidewall 16 between each of the lumens 30a in the first set of lumens provides space for placement of an opening 46b between adjacent lumens 30a and accessing one of the lumens 30b. An opening 46a is created through the sidewall 16 of hollow tube 15 so that the opening 46a is in fluid communication with the secondary lumen 30b. Likewise, an opening 46b is created through the sidewall 16 of hollow tube 15 so that the opening 46b is in fluid communication with the secondary lumen 30b. In one aspect, none of the lumens 30 may be in fluid communication with one another.

A flaccid, pressure-compliant member (e.g., a balloon 40, etc.) 40 is in fluid communication with each of the secondary lumens 30 (by way of a corresponding opening 46) and is positioned about the relatively non-compliant hollow tube 15 at a location corresponding to an opening 46. The pressure-compliant member 40, which is air-filled in one aspect, is structured to deflect or deform upon application of a force thereto, (e.g., an increase in pressure within the body cavity from the contraction of tissues within the body), and to expand again upon removal of the force therefrom (e.g., a subsequent decrease in pressure after a relaxation of the contracting tissues). Therefore, a particularly suitable pressure-compliant member 40 may be a medical grade balloon 40 formed of a thin-walled, flexible, low durometer material such as C-Flex® elastomer, which is relatively easily deformed with a small increase in pressure. In the aspect wherein numerous balloons 40 are disposed about the longitudinal axis of catheter 2, the catheter 2 provides for an increased number of points within the esophagus (or other body cavity) where measurements may be simultaneously taken. This improves the quality of testing done within the body and can shorten the length of the medical procedure.

The balloon 40 may have a generally spherical shape when inflated, though other shapes are contemplated within the present disclosure. The balloon 40 may be disposed about and attached to an opening 46 of a secondary (or monitor) lumen 30 and which is heat-sealed at the ends 42 of the balloon 40. Air occupies the interior of the secondary lumen 30 is at atmospheric pressure prior to use of the catheter 2. The secondary lumen 30 and the balloon 40 attached to the secondary lumen 30 (including any portion of the secondary lumen 30 that extends within the male connector 60) may, therefore, form or define an air column which extends from inside the male connector 60 to near the tip 14 of the catheter 2. When the catheter 2 is attached to a female connector, as explained further below, the air column becomes filled, or "charged," with an additional quantity of air. The additional air charged into the air column partially fills the balloon 40 to a selected volume. The material of the balloon 40 is very pliant due to its thin wall and the low durometer material used in its construction. As such, the balloon 40 deforms easily and substantially without artifact introduced by the material of the balloon 40 itself with a given change in pressure external to the balloon 40. The material of the balloon 40 may, for example, be about a 30 A Shore durometer hardness. A suitable material for use in forming the secondary lumen 30 may be C-Flex® synthetic elastomer of 1-2 mm wall thickness, or any other similar material having similar durability and flexibility or other material having characteristics suitable for the designs and use specified herein. Regardless of the material employed, less than 5 mm Hg of maximum external pressure should be required to collapse balloon 40 when its interior is vented to atmospheric pressure, though the balloon 40 is designed to be operable at pressure ranges ranging from 5 mm Hg to 200 mm Hg. The balloon 40 may be attached to an end of the secondary or monitor lumen 30 in any appropriate manner. However, the balloon 40 is attached to the secondary lumen 30 by positioning the balloon 40 over opening 46 of the secondary lumen 30 and securing the balloon 40 about the circumference of the opposing ends 48 of the balloon 40. The balloon 40 may be secured by laser welding, adhesive bonding, RF welding, induction welding, hot air welding, or other suitable methods for securing balloon 40 to the catheter 2.

In accordance with one aspect, a plurality of balloons 40 is formed from a unitary sleeve 41. For example, a single cylindrical sleeve 41 of flexible, low durometer material (e.g., PVC, elastomer, etc.) is disposed about an exterior of the hollow tube 15. The cylindrical sleeve 41 is secured to the body of the hollow tube 15 at different end points 42 along the longitudinal length of the sleeve 41 leaving a space between points of securement that are not secured to the hollow tube 15. The unsecured areas of the sleeve 41 between securement points 42 define the balloon 40.

In accordance with one aspect, a plurality of balloons 40 is formed from a unitary sleeve 41. For example, a single cylindrical sleeve 41 of flexible, low durometer material (e.g., PVC, elastomer, etc.) is disposed about an exterior of the hollow tube 15. The cylindrical sleeve 41 is secured to the body of the hollow tube 15 at different end points 42 along the longitudinal length of the sleeve 41 leaving a space between points of securement that are not secured to the hollow tube 15. The unsecured areas of the sleeve 41 between securement points 42 define the balloon 40.

Aspects of the current disclosure comprise air pressure monitoring within the esophagus (or other body cavity) of a patient. When used in connection with an esophageal motility study (EMS), a plurality of gas-filled pressure monitoring balloons 40 are disposed about a longitudinal length of the catheter 2. Once inserted within the esophagus of the patient, the pressure transducer 7 detects the change in pressure acting on the gas-filled balloon 40 as a patient swallows. In certain procedures, the gas-filled balloons 40 must be "zeroed" or calibrated before being "charged" with a volume of air and inserted into the patient. That is, any air entrained within a balloon 40 prior to being "charged" must be removed before charging to ensure that the balloon 40 is inflated to its calibrated volume.

In some embodiments, the catheter 2 may have electrical sensors to permit use of the manometry system of the present examples in impedance and/or other biological measurements such as EMG, ECG, pH and the like. In one aspect, sensor wires may extend through the central lumen 17 of catheter 2 and extend through apertures made through sidewall 16 of the catheter 2 to outside of the catheter 2, though in another aspect, the central lumen 17 is free of wires to facilitate bending and/or compression of the catheter 2. For instance, in such embodiments, a polyamide coated sensor wire or other electrically conductive member may be disposed in one or more monitor lumens 30 and extends from a proximal end 2a of the catheter 2 through the monitor lumens 30 to a terminating point along the longitudinal length of the catheter 2. On its proximal end, each of the wires is coupled to an electrical contact located in and/or coupled to an electrical connector. A corresponding electrical contact is located in and/or coupled to a cable assembly. In some embodiments, the sensor wire may terminate at a different longitudinal length about the catheter 2 and coupled to an electrode, electrical inductance sensor, or electrical impedance arrangement disposed about an exterior of the catheter 2. In some such embodiments, the electrical contacts and/or electrical connector of the catheter assembly can be connected to a software interface to facilitate transmission and/or display of electrical signals, measurements and the like to a user.

Continuing with the foregoing example, sensor wires disposed in the catheter 2 are connected to an impedance measuring system including a multichannel impedance transformer which serves to convert the impedances to be measured into a more conveniently recorded and displayed signal form, including a voltage or current signal. Signal outputs of a multichannel impedance transformer are applied to multichannel plotting or a recording device. Signal outputs may also be processed by a signal processor which may include further signal processing and display systems. In addition to the above mentioned impedance measurements, catheter 2 may be provided with one or more temperature measuring probes along its longitudinal axis for temperature measurements. Catheter 2 may also be used for receiving EMG signals which precede the mechanical contraction of an organ as well as simultaneous electrical function stimulation or excitation of the organ being examined. In one aspect, biosignal amplifiers and/or transducers can be connected to one or more sensor wires for the simultaneous reception of electrical biosignals such as pH, EMG and ECG signals. Similarly, current sources can be connected to sensor wires for electrical stimulation or activation of the organ being measured.

Figure 3:
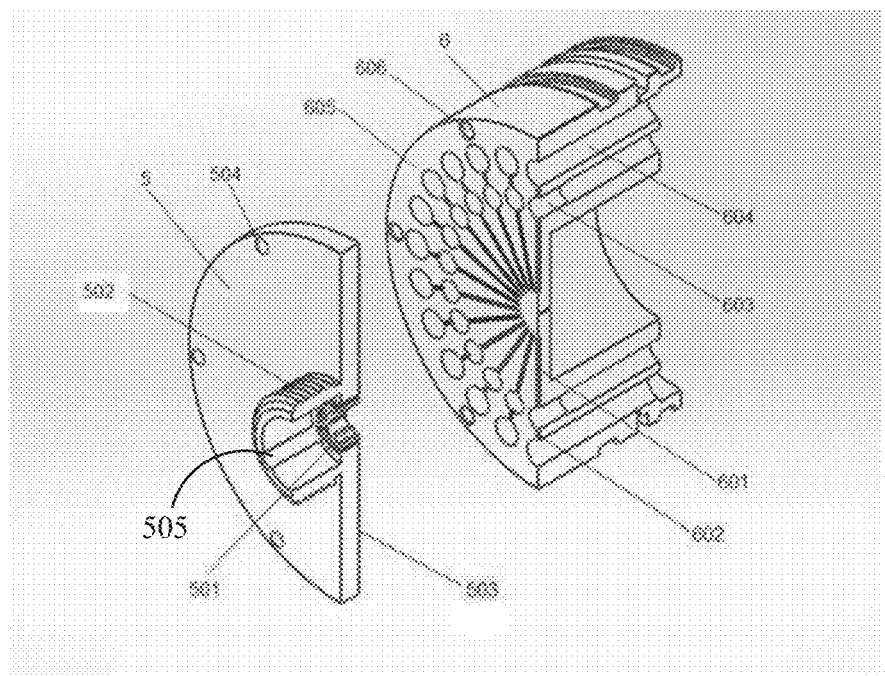
FIG. 3 illustrates a portion of FIG. 1B to show details of a connector subassembly.

Referring back to FIG. 1B, and referring now to FIG. 3, the multi-channel catheter connection system 1 comprises a connector sub-assembly 5, 6. The connector sub-assembly 5, 6 interfaces with the catheter sub-assembly 2, 3 and 4 as illustrated in FIG. 1B. For example, the connector sub-assembly 5, 6 and the catheter sub-assembly 2, 3, 4 can be assembled such that they are coaxially aligned. The physical coupling between the connector sub-assembly 5 and the catheter assembly provides the ability to measure pressure at various points in a patient lumen and improve measurement resolution, as will be described further below.

Figure 2F:
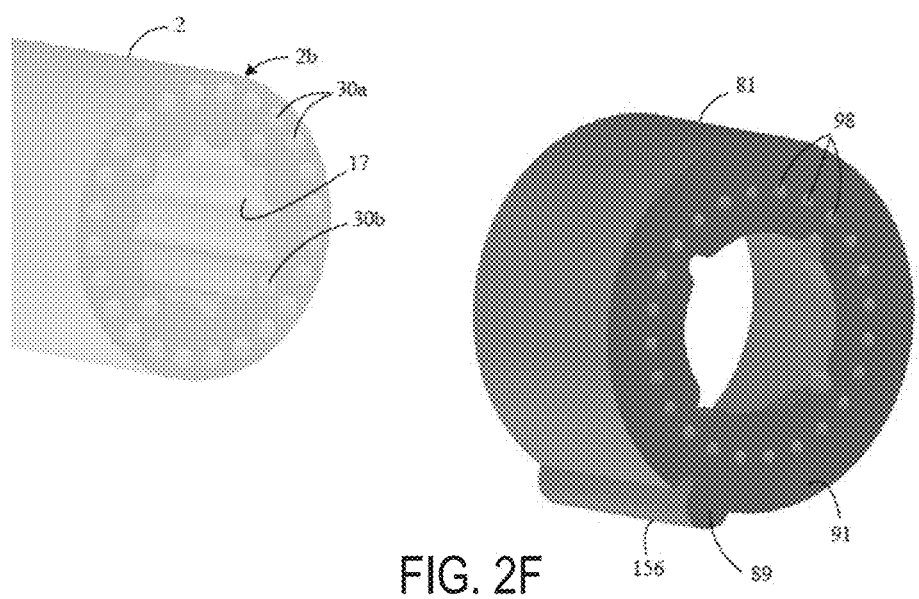
FIG. 2F is a perspective view of the proximal portion of the multi-channel catheter shown in FIG. 2B.

As seen in FIG. 3, the connector sub-assembly 5 comprises a front coupler 5 and a manifold block 6. The front coupler 5 receives catheter sub-assembly 2, 3, 4 at front housing 501 and locks the catheter sub-assembly 2, 3, 4 through complementary connection between threads 502 of the front coupler 5, and the threads 301 of the threaded cap 3 (best seen in FIG. 2A). Other connection methods, such as push fit, barbed connection and the like are also contemplated within the scope of the present disclosure (and as illustrated in FIG. 2F). In some such cases, as perhaps best seen in FIGS. 2A and 3, the front coupler 4 and the threaded cap 3 of the catheter 2 may include one or more alignment elements 505 to rotationally align the catheter sub-assembly 2 and the connector sub-assembly 5. For instance, the alignment element 505 in the illustrated embodiment is an alignment slot 505 on the front coupler 4 having a shape permitting insertion of a corresponding alignment element of the threaded cap 3 such that the catheter sub-assembly 2 and the connector sub-assembly 5 are rotationally aligned. The alignment element of the threaded cap 3 can be shaped and sized such that the threaded cap 3 may not be connectable (e.g., able to pass through the front coupler 4) if their respective alignment elements are not rotationally aligned.

The manifold block 6 comprises a plurality of longitudinal channels 603, 604 that are elongate in shape and disposed in a direction parallel to the central axis of the connector 6. The connector 6 also comprises a plurality of transverse channels 601, 602 fluidly coupled to the longitudinal channels 603, 604. The transducer housing 603 houses pressure transducers 7, while the charger housing 604 facilitates charging balloons 40 present on distal end 2b of the catheter 2 by way of a charging sub-assembly which will be described further below. The transducer housing 603 allows a pressure transmission medium to pass there through and reach a pressure transducer assembly 7 (best seen in FIG. 1B) for registering the pressure within a catheter pressure lumen 30 (best seen in FIG. 2B).

As is apparent from FIGS. 1B and 3, the front coupler 5 and the manifold block 6 are combined to form a sealed path along the transverse channels 601, 602 to allow the pressure transmission medium to pass through freely. For instance, the front coupler 5 and the manifold block 6 can be physically connected at end faces 503, 605 through mechanical means such as a screw-threaded connection through threaded holes 504, 606, bolts, or other fasteners.

Figure 4A:
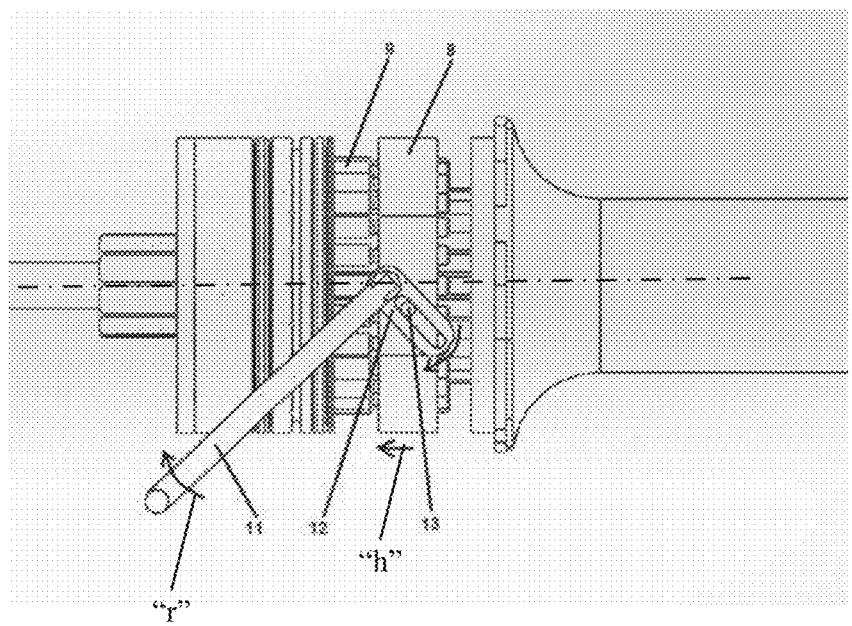
FIG. 4A illustrates a portion of FIG. 1A to show details of a charging mechanism, with the outer cover removed to illustrate interior detail.
Figure 4B:
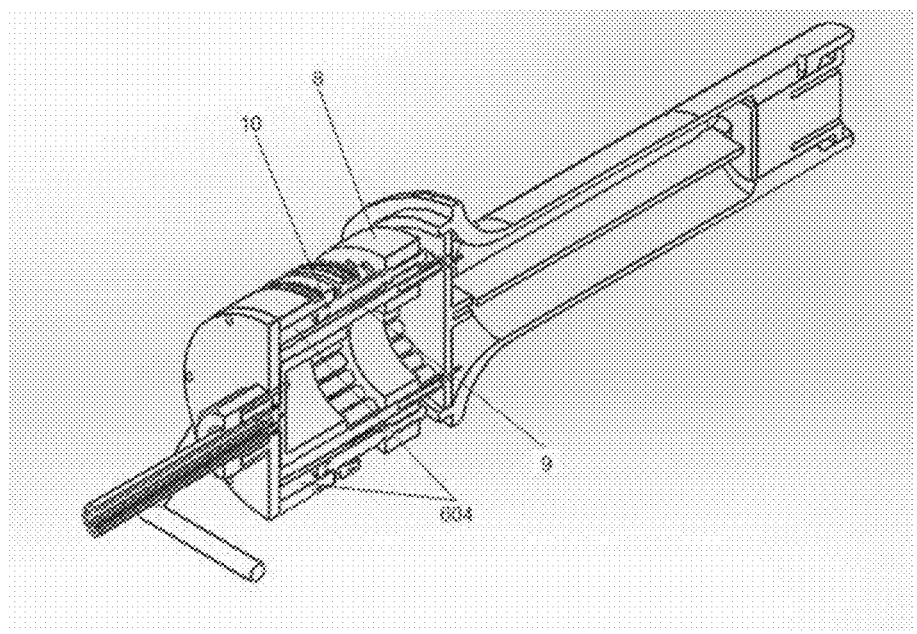
FIG. 4B is a sectional perspective view of charging mechanism of FIG. 4A.

Referring now to FIGS. 4A and 4B, the multi-channel catheter connection system 1 comprises a charging mechanism. The charging mechanism comprises a charger holder 8, and a plurality of charging piston 9 mounted thereon with a seal component 10 (e.g., O-rings). The charging pistons 9 can be moved within the charger housing 604 to charge the balloons 40 at the distal end 2b of the catheter 2 to facilitate pressure measurement.

Referring back to FIG. 4A, the charging mechanism comprises a handle 11 with an arm 12 to facilitate movement of the piston along the arrow "h" shown in FIG. 4A which would result in charging or discharging the catheter balloons 40 (e.g., with air). For instance, a linear movement of piston 9 in the charger housing 604 along the direction "h" can be accomplished by moving the handle 11 through arm 12 and pin 13 along the rotational direction "r" (e.g., by bringing the handle 11 toward the central axis). As a result of the physical connection between the handle 11 and arm 12, they rotate about a pivot at pin 13. Pin 13 is physically mounted on to charger holder 8, and as a result of the handle 11 rotation in the direction "r", the charger holder 8 moves horizontally along direction "h", while simultaneously moving the piston 9. While the above embodiment is provided as an illustrative example, alternative embodiments or modification may be made by those skilled in the art.

As shown in FIGS. 4C-4E, the handle 11 can be locked by rotating the handle 11 toward the central axis (shown by dashed lines) of the connector sub-assembly 5. Optionally, a sensor 1101 (e.g., a magnetic, mechanical or optical sensor) can be provided to confirm whether an end 1102 of the handle 11 that pivots about the pin 13 is in line with the sensor 1101, and consequently the handle 11 is locked. Once locked, the charger holder 8 moves, and the piston 9 translates horizontally along "h". Referring back to FIG. 1B, the translation of the piston 9 pushes an air column in the charger housing 604, into transverse channel 601 radially inward toward the catheter 2 to charge the catheter balloons 40. Referring back to FIGS. 2A and 3, as the handle 11 moves along the direction "h", end face 203 of the catheter 2 abuts the nips 401, while end face 403 of the connector 4 abuts against the end face 303 of the threaded cap 3. The cone 402 serves as an output orifice of the nips 401, and can sealingly engage with the pressure lumen 30 (e.g., squeezed/pressed into the pressure lumen 30) of the catheter 2 to form a sealed connection. Advantageously, the handle 11 is connected to the plurality of piston 9, facilitating moving multiple pistons 9 simultaneously. Such embodiments permit charging and discharging multiple balloons 40 simultaneously, permitting higher measurement resolution using multiple transducers, while reducing measurement time (e.g., instead of charging and discharging each balloon 40 separately). Further, embodiments disclosed herein are of a compact construction by housing the plurality of pistons and charging mechanisms within a single charger holder 8. Other charging mechanisms, such as a rotary threaded piston, or other charging mechanisms are also within the scope of the present disclosure.

Referring now to FIG. 5, the multi-channel catheter connection system 1 comprises a pressure transducer 7 with a plurality of pressure sensors 701 in communication with a pressure transmission medium (e.g., fluids) flowing through the charger housing 604 between charging piston 9 and catheter lumen 30. As described above, the pressure transducer 7 resides in the transducer housing 603 and the charging piston 9 charger housing 604. The pressure transducer 7 and charging piston 9 are in free communication with each other through the sealed path formed by transverse channels 601, 602 from catheter pressure lumen 30 to the charger housing 604.

With continued reference to FIG. 5, the pressure transducer 7 comprises a pressure sensor 701, electrical leads 702 and housing 703. The pressure sensor 701 in the illustrated embodiment can be arranged in the front end of a housing of the pressure transducer 7. Further, referring back to FIGS. 1B, 3 and 5, the pressure sensor 701 is housed so as to be in contact with charger housing 604 between charging piston 9 and catheter lumen 30. Electrical leads 702 are provided on an end of the pressure transducer 7 opposite to the pressure sensor 701. The electrical leads 702 may be electrically connected to an electrical connector sub-assembly 31, 31 which will be described further below.

Figure 6:
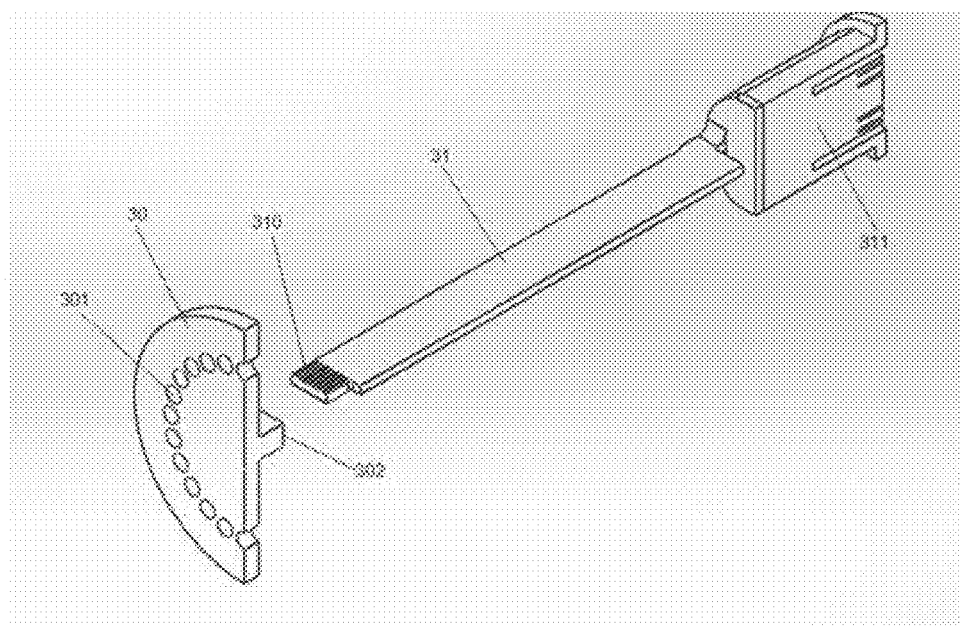
FIG. 6 is a perspective view of electrical connector sub-assembly.

Referring now to FIG. 6, the multi-channel catheter connection system 1 comprises an electrical connector sub-assembly 31 for transmitting electrical signals from the pressure transducer 7 to an output. The electrical connector sub-assembly 31 is housed in a housing 50 and comprises an electrical connection adaptor 31 that receives and holds the plurality of pressure sensor transducers 7 in cavities 301 and converts the electrical output leads 702 into a connector terminal 302 (e.g., a female terminal) which can be coupled to a complementary (e.g., a male terminal) connector 310 of an electrical output connector 31. The output connector 31 can have electrical connector terminals 311 for connecting to various types of medical instruments. Further, the electrical connector sub-assembly 31, 31 may further include an electrical port for receiving other electronic signals such as EMG, ECG, bio-impedance, pH measurement signals from the catheter sub-assembly 2.

In use, the air-charge system can measure the pressure of an anatomical patient lumen (such as stomach, esophagus, bladder, or rectum). The catheter 2 can first be inserted into the patient lumen. The catheter 2 can then be connected by threaded cap 3, connector 4, and front coupler 5. The pressure sensing balloons 40 can be simultaneously charged by moving the handle 11 toward the central axis of the catheter 2, and locking the arm 12 in place. When locked as such, the pressure sensing balloons 40 (not shown) may be in contact with an interior wall of the patient lumen. The pressure transducers 7 are in fluid communication with the transverse channel 601 (through transverse channel 602), as a result of which, the pressure from the balloons 40 is transmitted back to the pressure transducer 7 housed in the transducer housing 603. When the pressure measurement is complete, the pressure sensing balloons 40 can all be discharged simultaneously by moving the handle 11 in opposite direction and unlocking the arm 12, after which the catheter 2 can be withdrawn from the patient. Optionally, the catheter 2 can be discarded, while the connector sub-assembly 5 can be reused.

Figure 7:
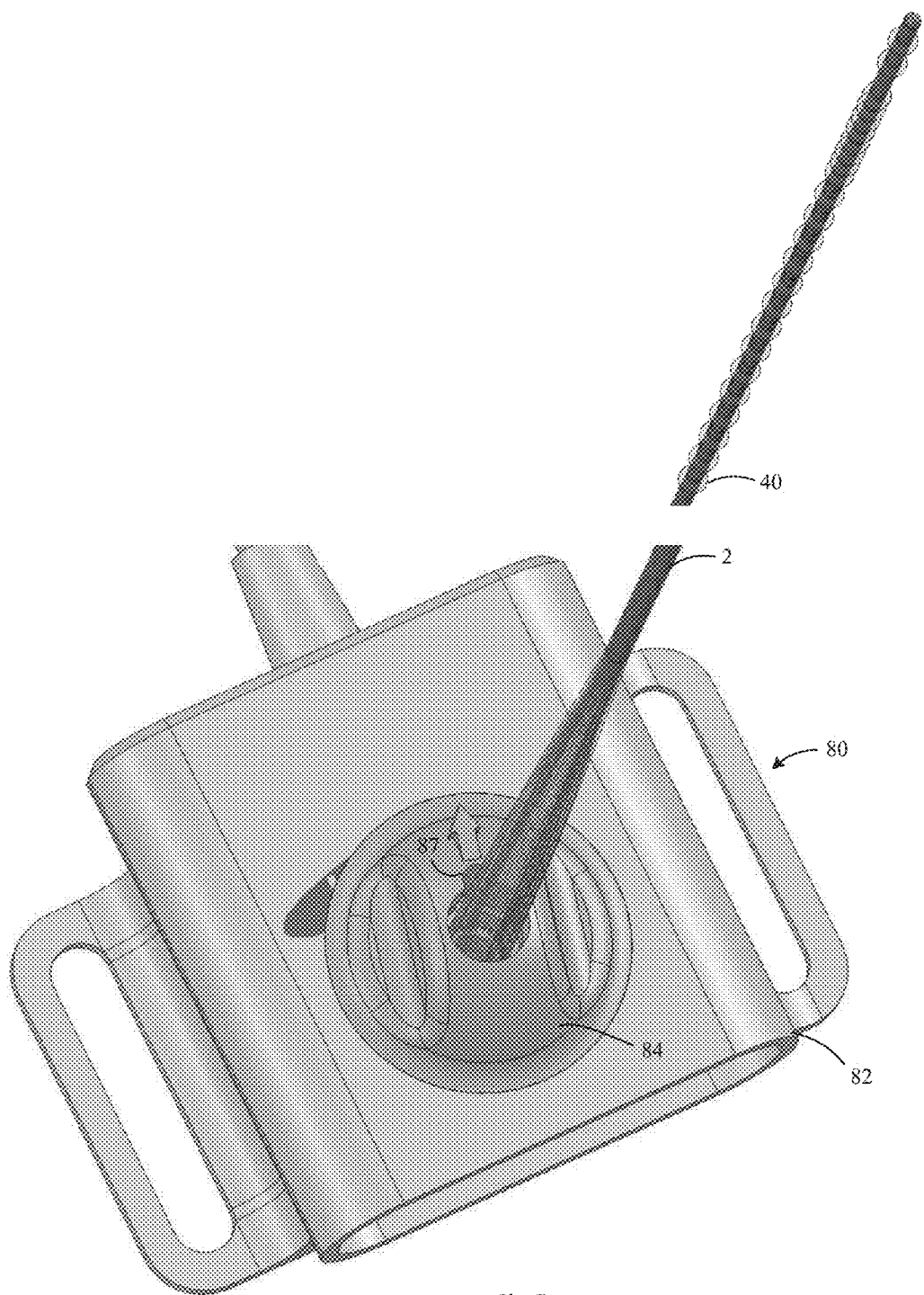
FIG. 7 is a perspective view of a connector assembly according to another example.
Figure 8:
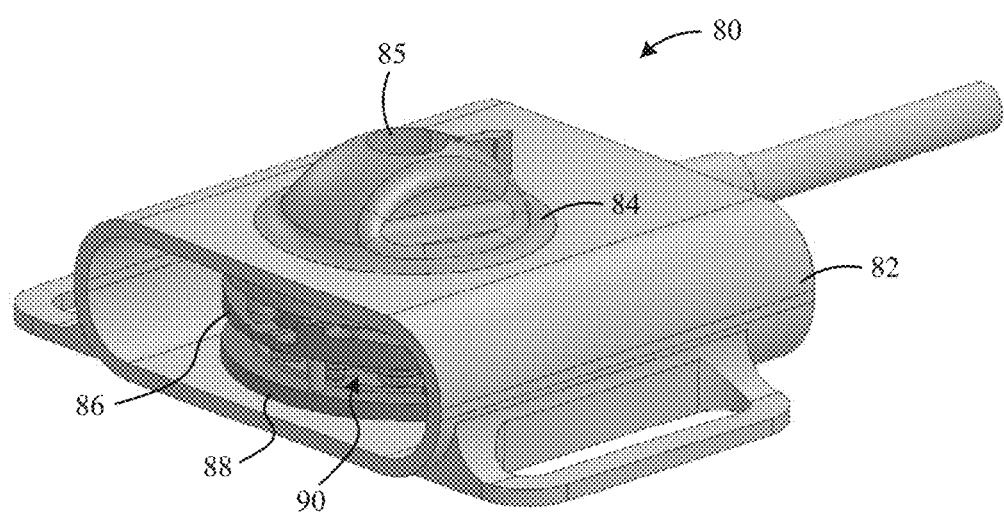
FIG. 8 is a perspective view of the connector assembly of FIG. 7 shown without the catheter assembly.
Figure 9:
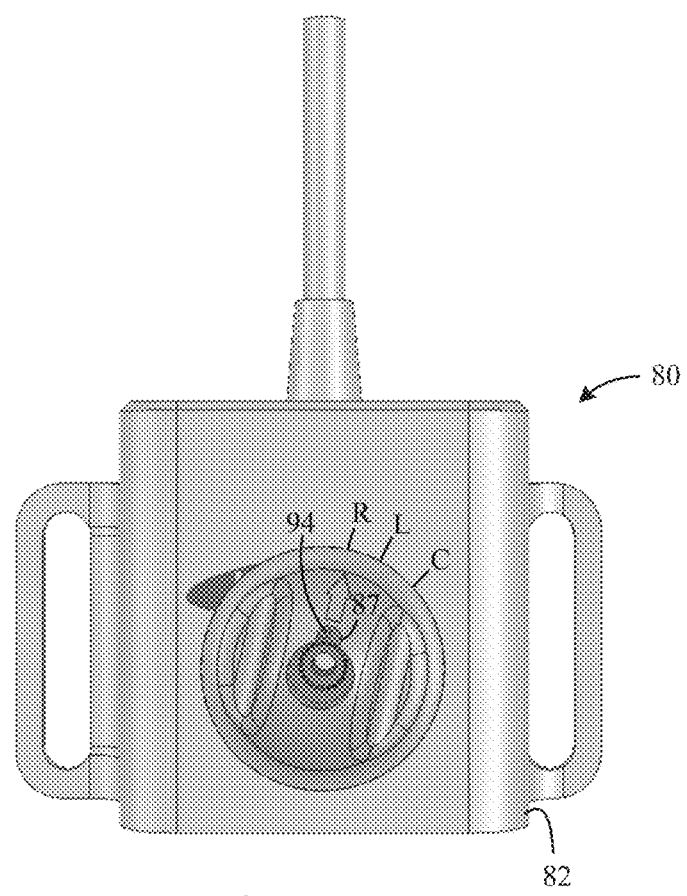
FIG. 9 is a top plan view of the connector assembly of FIG. 8.

FIGS. 7-18 illustrate a connector assembly 80 for an anatomical manometry system according to another example. As was the case with the system illustrated in FIGS. 1-6, the catheter sub-assembly 2 of FIGS. 2C-2F and described herein can be used with the connector assembly 80. As was the case with the connector sub-assembly 5 of FIGS. 1-6, the connector assembly 80 shown in FIGS. 7-18 can be connected with the proximal end 2a of the catheter 2. Further, in the illustrated embodiment of FIG. 7-18, however, the catheter 2 has a proximal coupler 81 (best seen in FIG. 2F) similar to the front coupler 4 illustrated in FIGS. 2A-2B. While FIG. 7 illustrates the connector assembly 80 with a catheter 2 connected thereto, FIGS. 8 and 9 illustrate the connector assembly 80 without a catheter 2.

Figure 10:
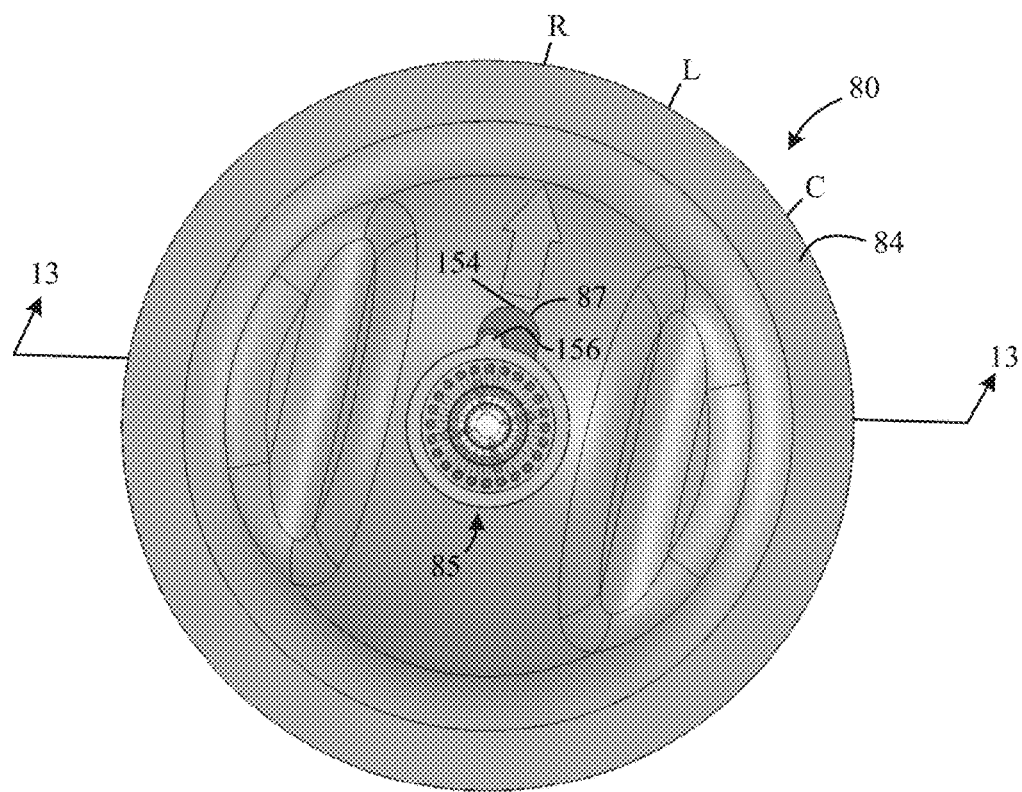
FIG. 10 is a top plan view of the connector assembly of FIG. 8 shown without its outer housing.

FIG. 10 illustrates a top view of the connector assembly 80 shown without the outer housing 82. The connector assembly 80 comprises a connector interface 84 connectable to the proximal end 2a of the catheter 2 and is coaxially aligned therewith. The connector interface 84 has a central aperture 85 configured for receiving the proximal end 2a of the catheter 2, and the proximal coupler 81 connected thereto. The connector assembly 80 also comprises a manifold 86, a sensor assembly 88 and a charging mechanism 90.

As seen in the illustrated example, the connector interface 84 can have an alignment element 87 to permit alignment between the catheter 2 and the connector interface 84. For instance, the alignment element in the illustrated embodiment is an alignment slot 87 having a shape permitting insertion of a corresponding alignment element of the proximal coupler 81. In such examples, as seen in FIG. 2F, the proximal coupler 81 has an alignment key 89 that can be received within and through the alignment slot 87, when the proximal coupler 81 and the connector interface 84 are rotationally aligned. The alignment element of the connector interface 84 can be shaped and sized to block the proximal coupler 81 from passing therethrough if the proximal coupler 81 and the connector interface 84 are not rotationally aligned.

Referring now to FIG. 11, a cross-sectional view of the connector assembly 80 with a catheter 2 connected thereto is illustrated. As seen therein, the connector assembly 80 includes a manifold 86 fluidly coupled to the catheter 2 by a complementary connection with the connector interface 84. The manifold 86 is coaxially and rotationally aligned with the proximal coupler 81 such that a bottom surface 91 of the proximal coupler 81 is seated in contact with and above the top surface 92 of the manifold 86. In the illustrated embodiment, the alignment key 89 of the proximal coupler 81 protrudes past the bottom surface 91 of the proximal coupler 81 so as to be received within a recess 94 defined on the top surface 86C of the manifold 86. As is apparent from the cross-sectional view of FIG. 11, once the proximal coupler 81 is received within the recess 94 and rotationally aligned with the manifold 86, the proximal coupler 81, and consequently the catheter 2 may not rotate relative to the manifold 86 when the connector interface 84 is rotated thereafter, and remain rotationally stationary during use. However, the connector interface 84 may rotate relative to the catheter interface and/or the manifold 86.

Referring again to FIG. 10, the connector interface 84 may rotate into one of three rotational positions: a release position "R", a locked position "L", and a charged position "C". For instance, as seen in FIG. 10, when the connector interface 84 is in the release position "R" the alignment slot 87 and the alignment key 89 are aligned with each other, and a bottom portion of the alignment key 89 is received within the recess 94. In this position, the catheter 2 may be released from the connector assembly 80 (e.g., by lifting the catheter assembly away from the connector assembly 80). Rotation of the connector interface 84 about the center axis may move it from the release position "R" to the locked position "L". In the locked position "L", as the alignment key 89 is not aligned with the alignment slot 87 the catheter assembly may not be removable from the connector assembly 80. As used herein, the term "aligned" when used in the context of the alignment element may refer to a situation whereby the alignment elements of the connector interface 84 and catheter assembly are generally of a complementary shape to permit the connector interface 84 and the catheter assembly to be rotationally aligned. In some such embodiments, the electrical contacts and/or electrical connector of the catheter assembly can send electrical signals to provide feedback on the rotational position of the knob "R", "L" or "C" to a user or an operator via a software interface. Advantageously, such embodiments may allow a user or an operator to confirm status of knob without necessarily visually looking at it.

Referring to FIGS. 11-14, the manifold 86 comprises as a plurality of axial channels 96 oriented in a direction parallel to the central axis "O" of the catheter. Referring again to FIG. 11, each axial channel of the manifold 86 is aligned with and fluidly coupled to a respective opening 98 (e.g., through nips 401 inserted into the openings 98) on the proximal coupler 81, which in turn is axially aligned with and fluidly coupled to a catheter lumen 30 when the catheter 2 is connected to the connector interface 84 and rotationally aligned therewith. Accordingly, in some embodiments, when the catheter 2 is connected and rotationally aligned with the connector interface 84, each axial channel of the manifold 86 is fluidly coupled to a catheter lumen 30. As described previously, each catheter lumen 30 may be fluidly coupled to a balloon 40. Thus, when connected, each axial channel may be fluidly coupled (e.g., indirectly, via the openings 98 on the proximal coupler 81 and catheter lumen 30) to a respective balloon 40. Such connections may permit charging (e.g., supplying a pressure transmission medium) through the fluid couplings of the manifold 86 and the catheter lumen 30 to inflate a balloon 40 and thereby receive a pressure reading from a patient lumen.

Figure 13:
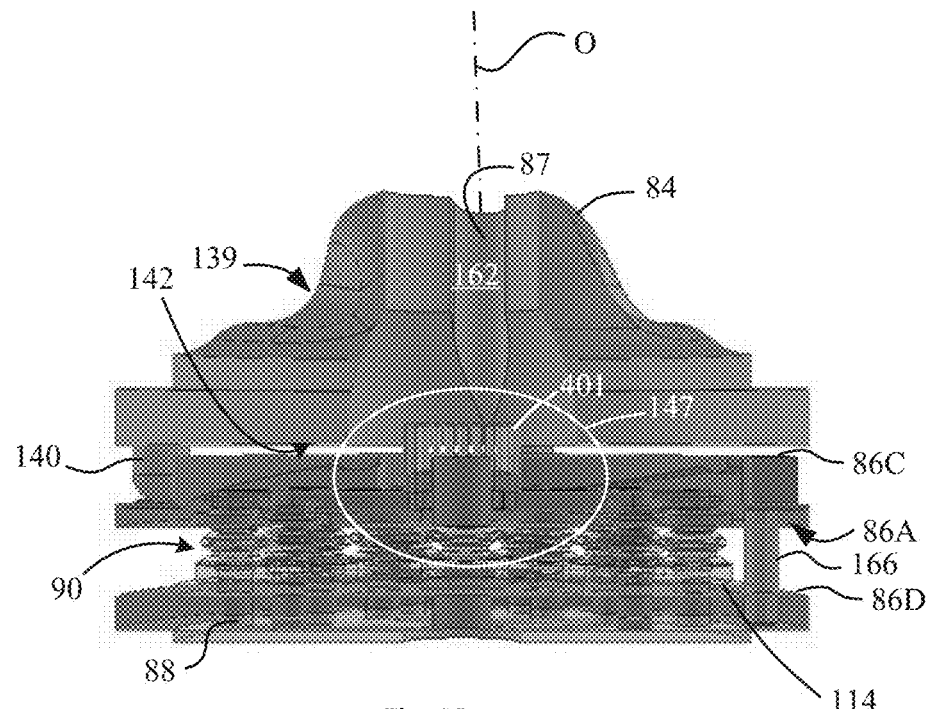
FIG. 13 is a sectional perspective view of the connector assembly of FIG. 8 taken along plane 13-13.
Figure 14:
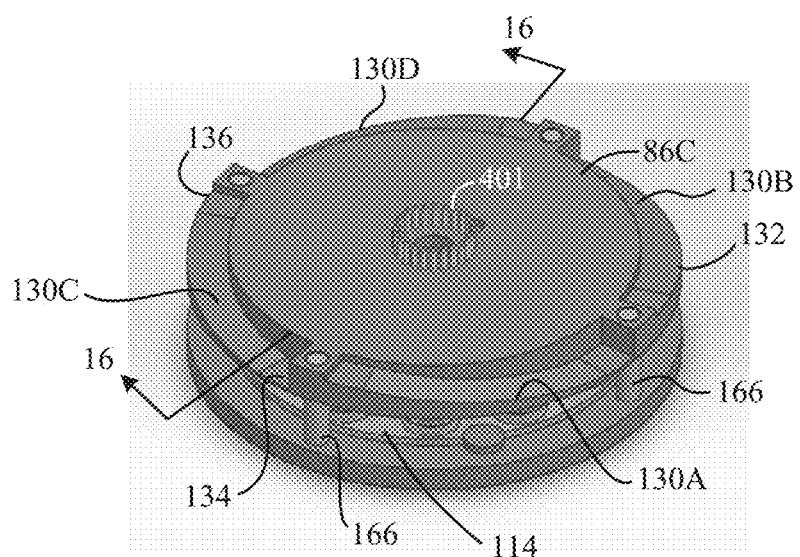
FIG. 14 is a sectional perspective view of a manifold and a charging assembly of the connector assembly of FIG. 8.
Figure 15:
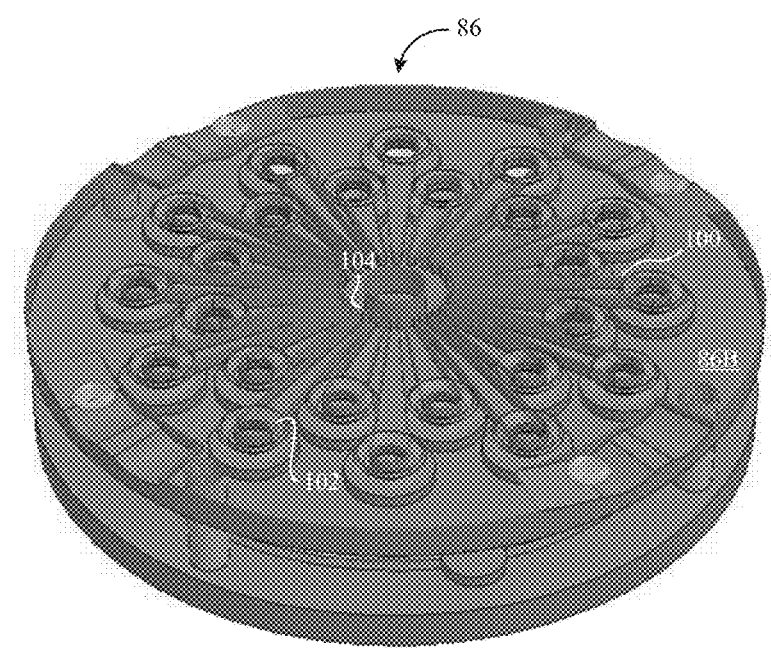
FIG. 15 is a sectional perspective view of the manifold and charging assembly of FIG. 14.
Figure 16:
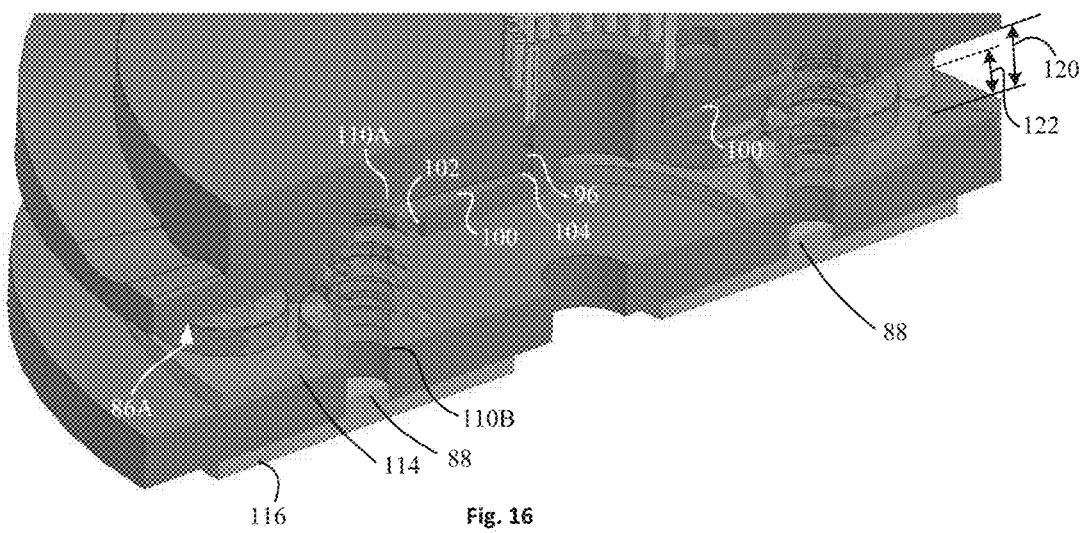
FIG. 16 is an enlarged cross-sectional view of the manifold and charging assembly of FIG. 14.

FIG. 15 is a top perspective view of the manifold 86 and FIG. 16 is an enlarged sectional view of portion 17 of the manifold 86 seen in FIG. 13. As seen from these two drawings, the manifold 86 includes a plurality of radial channels 100 oriented in a radial direction (and perpendicular to the central axis of the connector assembly 80). As used herein, the term "radial direction" may include directions that are along a radius, for instance, along a direction connecting the center of the manifold 86 and an outer perimeter 132 of the upper surface 86C of the manifold 86. Further, the term "radial direction" may also include a channel disposed in the manner of a pinwheel with slight offsets from a radius of the upper surface 86C of the manifold 86. As seen from FIGS. 15-16, the radial channels 100 are defined on an interior surface 86B of the manifold 86 in a plane perpendicular to the center axis "O", whereas the axial channels 96 are defined at least partially within the body portion of the manifold 86. Each radial channel 100 is fluidly coupled to a respective axial channel, and correspondingly fluidly connected (e.g., indirectly) to a balloon 40 (e.g., via the openings 98 on the proximal coupler 81 and catheter lumen 30). As will be described further below, the radial channels 100 can be fluidly coupled to a charging mechanism 90 so as to permit passage of a pressure transmission medium therethrough and toward the balloons 40.

In some exemplary embodiments, each radial channel 100 may generally taper along the radial direction. Such an embodiment permit connecting a charging mechanism (described below) to a catheter lumen. For example, as seen in FIG. 15, the radial channels 100 taper toward the central axis "O". Each radial channel 100 comprises a first radial opening 102 and a second radial opening 104. The first radial opening 102 is positioned further away from the central axis relative to the second radial opening 104. Further, the first radial opening 102 has a first radial opening 102 size and the second radial opening 104 has a second radial opening 104 size, the first radial opening 102 size being greater than the second radial opening 104 size. In the illustrated embodiment, the first radial opening 102 and the second radial opening 104 are each generally circular in shape. The first radial opening 102 has a diameter greater than the diameter of the second radial opening 104. As seen in FIG. 16, the second radial opening 104 is coupled to a respective axial channel, and has an opening diameter generally corresponding to (e.g., equal to, slightly greater than, or slightly less than) the diameter of the axial channel. The first radial opening 102 on the other hand, is sized to connect to a charging mechanism 90 as described below.

Referring back to FIG. 12A, the manifold 86 comprises a charging mechanism 90 for charging the balloons 40. As was the case with the exemplary embodiment of FIGS. 1-6, the charging mechanism 90 can commonly charge individual balloons 40. For instance, the charging mechanism 90 can be commonly actuated to simultaneously charge each individual balloon 40, as will be described below.

Figure 17:
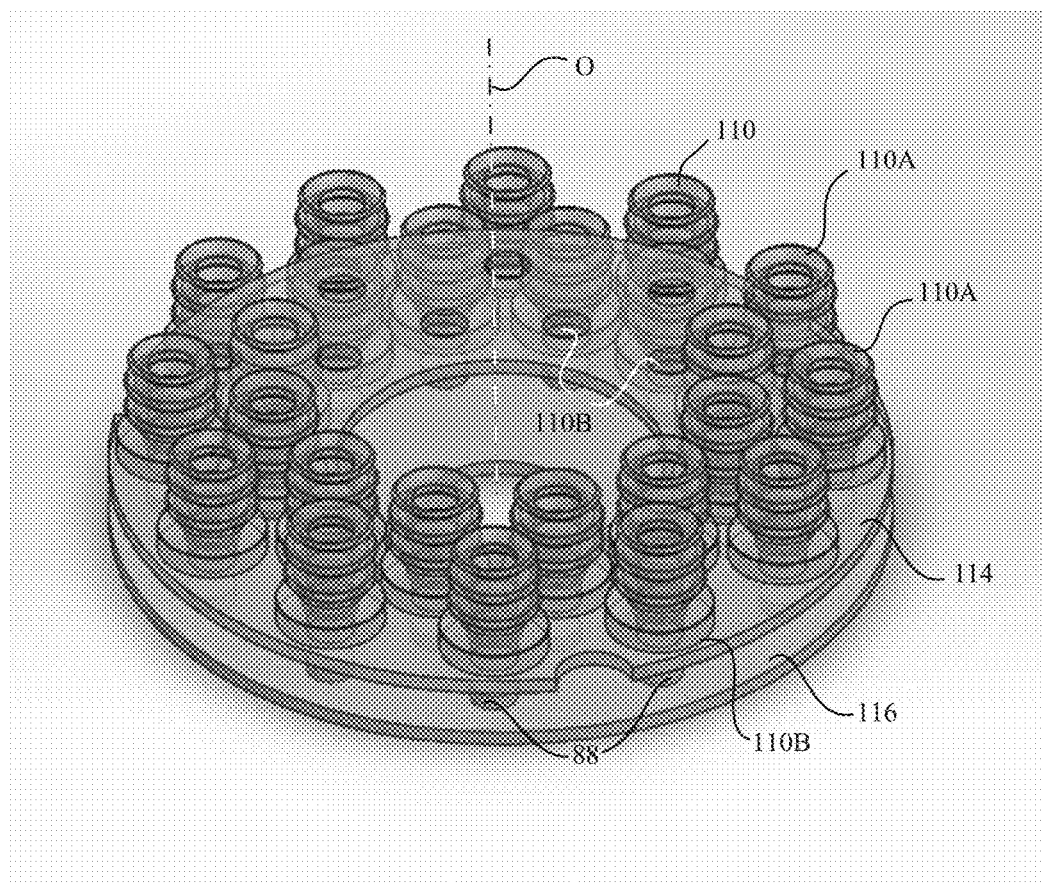
FIG. 17 is a perspective view of the charging assembly shown in FIG. 14.

As seen in FIGS. 11 and 16, the charging mechanism 90 comprises a plurality of bellows 110. Each bellow can be fluidly coupled to a respective radial channel 100, a respective axial channel, a respective catheter lumen (best seen in FIG. 11), and in turn, a respective balloon 40 (not shown in FIGS. 11 and 16). When connected, the bellows 110 may permit passage of the pressure transmission medium from the charging mechanism 90 toward the catheter lumen. The bellows 110 can compress axially along the central axis "O" to transmit the pressure transmission medium and thereby charge the balloons 40. As seen in FIG. 17, the bellows 110 are arranged surrounding the central axis at various radial distances corresponding to the location of the first radial opening 102 of each radial channel 100. For instance, as seen in FIGS. 16 and 17, each bellow has a first end 110A and a second end 110B, whereby the first end 110A of the bellow is coupled (directly or indirectly so as to permit passage of the pressure transmission medium) to the first radial opening 102 of a respective radial channel 100. The manifold 86 can include apertures 112 at locations corresponding to the radial position of the first end 110A of the bellows 110 so as to permit the bellows 110 to contact and/or pass through at least a first surface 86A of the manifold 86. The first surface 86A, for instance, can be bottom surface and/or a surface that is spaced from (e.g., opposite to) the surface 86B on which the radial channels 100 are defined. As perhaps best seen in the enlarged view of FIG. 16 the first end 110A of the bellows 110 passes through the apertures 112 on the manifold 86, and remain in contact with the first opening 102 of each radial channel 100.

The bellows 110 are commonly actuable when the manifold 86 is connected with the connector interface 84 to permit simultaneously charging each balloon 40 of the plurality of balloons 40. For instance, as seen in FIG. 17, in the illustrated exemplary embodiment, the bellows 110 are commonly-housed on a bellow housing 114 such that the second end 110B of each bellow contacts the bellow housing 114. The second end 110B of the bellow is axially opposite to the first end 110A and may be connected (e.g., directly or indirectly) to a pressure transducer housing 116 for sensing pressure of the balloons 40 fluidly coupled to each bellow. The bellow housing 114 can be coaxial with the central axis of the catheter 2 whereby each bellow has a bellow axis parallel to the central axis of the catheter 2.

In some examples, the manifold 86 and the bellow housing 114 are separated by a first axial distance 120 when the catheter 2 is disconnected from the catheter 2 interface, whereas, the manifold 86 and the bellow housing 114 are separated by a second axial distance 122 (illustrated by dashed lines) when the catheter 2 is connected to, locked with the connector interface 84 and charging has commenced. The second axial distance 122 can be less than the first axial distance 120. This may correspond to a state where the bellows 110 are "compressed" so as to charge the balloons 40. For instance, the compression of the bellows 110 may result in pressuring and supplying a fluid pressure transmission medium toward the balloons 40, thereby causing the balloons 40 to be charged.

Referring back to FIGS. 12A-14, compression of bellows 110 may be achieved by a complementary connection between the proximal coupler 81 of the catheter 2, the manifold 86 and the connector interface 84. For instance, the manifold 86 may be rotationally connected with the connector interface 84 by a rotationally complementary connection. Such a connection may permit rotation of at least one of the connector interface 84 and the manifold 86 with respect to another. For instance, the manifold 86 (and the proximal coupler 81 connected thereto) may remain stationary with respect to the connector interface 84, whereas the connector interface 84 may be free to rotate about the center axis. The rotation of the connector interface 84 relative to the manifold 86 may permit an axial displacement of the manifold 86 relative to the bellow housing 114 so as to simultaneously actuate each bellow positioned on the bellow housing 114. Prior to the axial displacement, the manifold 86 and the bellow housing 114 may be separated by a first axial distance 120, and following the axial displacement, the manifold 86 and the bellow housing 114 may be separated by a second axial distance 122 (less than the first axial distance 120).

FIGS. 12A-14 illustrate an exemplary complementary connection between the manifold 86 and the connector interface 84. As illustrated therein, the manifold 86 includes a ramp portion 130 defined near an outer perimeter 132 thereof. The ramp portion 130 may include one or more ramp surfaces 130A, 130B, 130C, 130D, etc. Each ramp surface 130 may curve along the outer perimeter 132 of the manifold 86 and follow its contours about the center axis "O". Each ramp surface 130 may include a first ramp surface end 134 and a second ramp surface end 136 circumferentially opposite thereto. The first ramp surface end 134 and the second ramp surface end 136 can be separated axially and/or disposed on different axial planes.

Figure 12A:
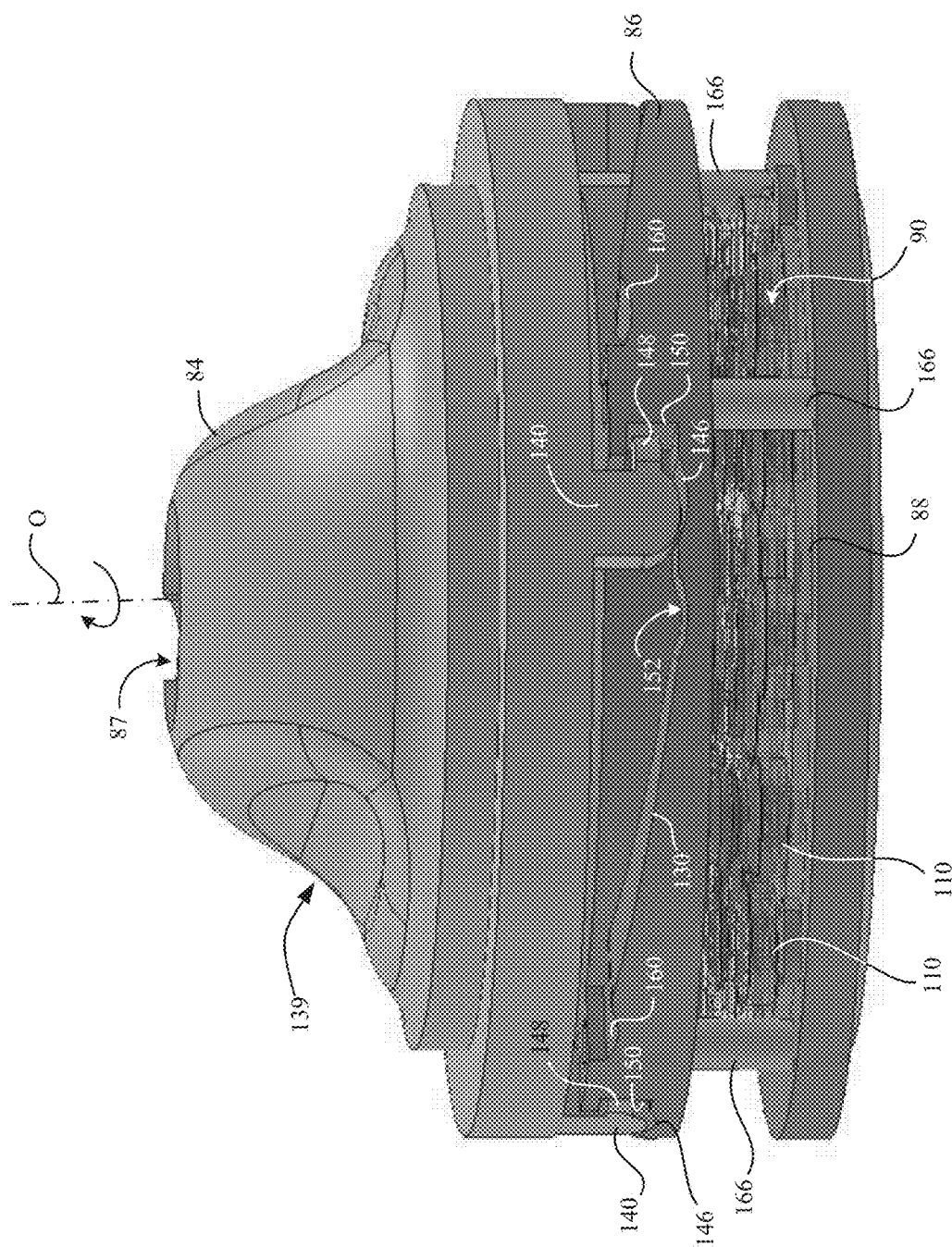
FIG. 12A is another perspective view of the connector assembly of FIG. 8.
Figure 12B:
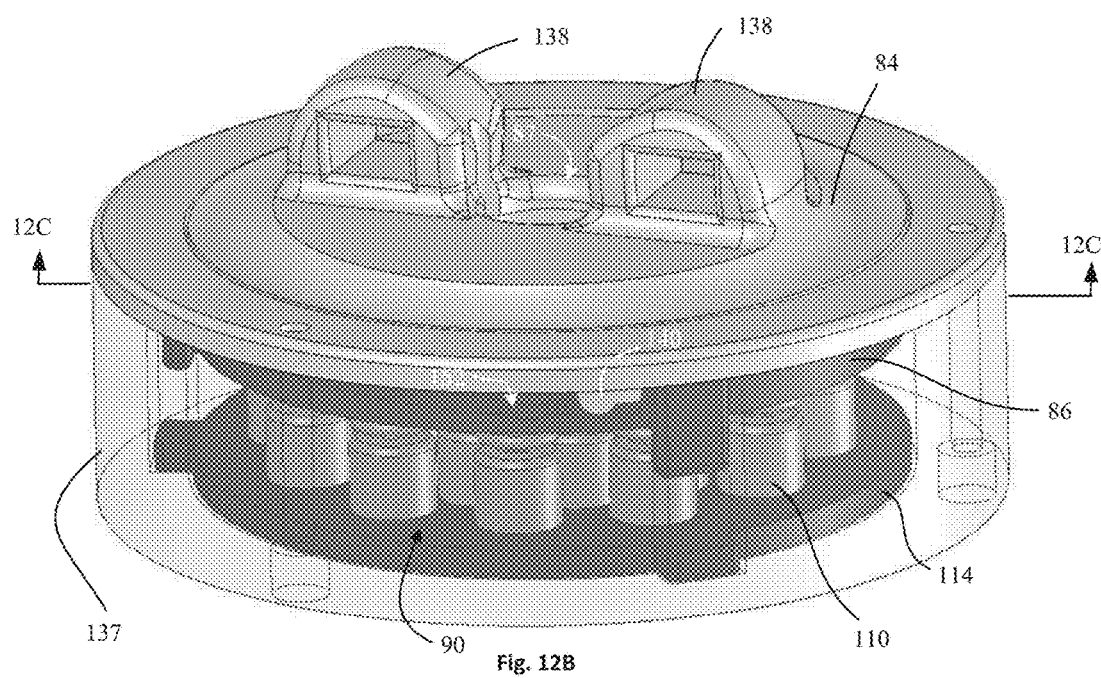
FIG. 12B is a perspective view of the connector assembly according to another embodiment.
Figure 12C:
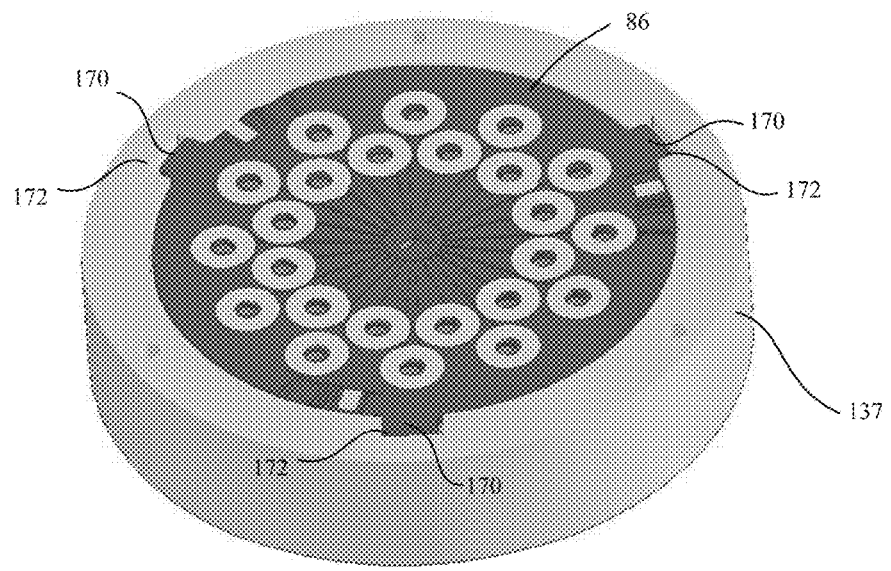
FIG. 12C is a sectional perspective view of the connector assembly of FIG. 12B taken along the line 12C-12C.

FIGS. 12B and 12C illustrate another exemplary embodiment of the connector assembly. The connector assembly as shown in FIGS. 12B and 12C is substantially similar to the embodiment of FIG. 12A, with the exceptions described herein. In FIGS. 12B and 12C, the connector assembly has an outer cover 137 that substantially encloses the manifold, the charging mechanism and transducer housing. As seen from FIGS. 12B and 12C, the outer cover 137 has a diameter greater than the diameter of the manifold, such that the manifold is enclosed within the outer cover 137. The outer cover 137 may be a physically separate component from the connector interface 84 such that when the connector interface is rotated to charge the charging mechanism (as will be described further below), the outer cover 137 remains rotationally stationary relative to the connector interface 84. Further, advantageously, in the embodiments of FIGS. 12B and 12C, the connector interface may optionally include finger grasps 138 (instead of support surfaces 139 of FIG. 12A) to permit an operator to apply torque on to the connector interface 84 to rotate it relative to the manifold 86 and charge the charging mechanism.

As seen in FIGS. 12A and 13, the connector interface 84 may include one or more pins 140 that may travel along a corresponding ramp surface 130 of the manifold 86. The pins 140 protrude from a bottom surface 142 of the connector interface 84 toward the manifold 86. Accordingly, in one example, the rotationally complementary connection comprises engagement of the plurality of pins 140 with the ramp portion 130 of the manifold 86. For instance, as the connector interface 84 is rotated about the center axis "O", the pins 140 may travel in a circumferential direction 144 (as illustrated in FIG. 12A), along the ramp surface 130.

Referring to FIGS. 10 and 12A, initially, when the catheter 2 is in the "release position" and/or not connected to the connector interface 84, the pin 140 may rest against a first dimple 146 on the ramp portion 130. In this location, the pin 140 may have protrusion 148 that extends in a direction perpendicular to the direction in which the pin 140 extends and/or perpendicular to the center axis. The protrusion 148 may be received in a corresponding recess 150 on the manifold 86. In this position, the manifold 86 is "locked" with respect to the connector interface 84 such that relative axial motion between the manifold 86 and the bellow housing 114 is reduced and/or prevented. Advantageously, in some such examples, if the catheter 2 were to be brought toward the connector interface 84 and pressed to engage therewith (e.g., such that the nips 401 on the manifold 86 are received in corresponding apertures 98 of the proximal coupler 81), any force associated with the connection of the catheter 2 to the connector interface 84 may not prematurely compress the bellows 110.

When the connector interface 84 is in the release position "R", the alignment slot 87 and the alignment key 89 are aligned with each other, and a bottom portion of the alignment key 89 is received within the recess 94. In this position, the catheter 2 may be released from the connector assembly 80 (e.g., by lifting the catheter assembly) away from the connector assembly 80.

As the pin 140 moves from the first end 110A to the ramp surface 130 to the second end 110B (e.g., along rotational direction 144), the connector interface 84 may move from the release position "R" where the catheter assembly is releasable from the connector assembly 80 to the locked position "L" where the catheter assembly is locked with respect to the connector interface 84. At this location, the pin 140 may rest against the second dimple 152. Such embodiments facilitate providing haptic feedback to an operator that the catheter assembly is locked with respect to the connector interface 84, and that further rotation of the connector interface 84 (e.g., along rotational direction 144) may cause the bellows 110 to be compressed, and charging of the balloons 40 may commence.

Referring back to FIG. 10, the rotational complementary connection between the manifold 86 and the connector interface 84 described above results in an interference fit and/or a cam effect between the alignment key 89 of the proximal coupler 81 and the alignment slot 87 of the connector interface 84. When the connector interface 84 is in the locked position "L" (and rotated further from the release position "R"), the pin 140 rests in the second dimple 152. In this position, as perhaps best seen in FIG. 13, the alignment slot 87 may not extend an entire distance till the bottom surface 142 of the connector interface 84, thereby having a clearance along the center axis "O" between the alignment key 89 and the alignment slot 87. As a result, the catheter 2 may not twist relative to the manifold 86, even though the connector interface 84 rotates relative to the manifold 86. As a result, the alignment slot 87 is not aligned with the alignment key 89 when in the locked position "L" as is apparent from FIG. 10. For instance, an apex 154 of the alignment key 89 and an apex 156 of the alignment slot 87 are at different rotational positions (e.g., not in line with each other). Accordingly, the catheter assembly may not be removable from the connector assembly 80. Further rotation of the connector interface 84 with respect to the manifold 86 results in interference between the alignment slot 87 and certain portions of the alignment key 89.

Further rotation of the connector interface 84 with respect to the manifold 86 along the rotational direction 144 may correspondingly move the pin 140 further along the ramp surface 130, toward the second ramp surface end 136. The pin 140 may rest against a third dimple 160. As is apparent, the first dimple 146 and third dimple 160 of each ramp surface 130 are circumferentially opposite to each other, however, each ramp surface 130 has its first dimple 146 proximal to the third dimple 160 of an adjacent ramp surface 130. At this position, the interior surfaces 162 of the alignment slot 87 may act as a cam with respect to the alignment key 89. As described previously, in some such embodiments, the electrical contacts and/or electrical connector of the catheter assembly can send electrical signals to provide feedback on the rotational position of the knob to a user or an operator via a software interface. Advantageously, such embodiments may allow a user or an operator to confirm status of knob without necessarily visually looking at it.

In some examples, the manifold 86 may include a plurality of guide post 166, whereby each guide post 166 is positioned between first dimple 146 of a ramp surface 130 and a third dimple 160 of an adjacent ramp surface 130. The guide post 166 extends through corresponding holes 168 on the manifold 86 (e.g., on surfaces 86A and 86D) and sensor plate. The guide post 166 may permit components other than the connector interface, such as manifold, the pressure transducer housing and charging mechanism to remain rotationally stationary when the connector interface rotates about the axis "O". As described previously, the connector interface 84 therefore rotates relative to the manifold. When the connector interface 84 is rotationally twisted with respect to the manifold 86 such that a pin 140 of the connector interface 84 travels on a ramp surface 130 of the manifold 86, resulting force associated with this motion is transmitted by the guide post 166, so as to compress the manifold 86 with respect to the bellow housing 114. As the manifold 86 is axially moved relative to the bellow housing 114, the guide post 166 may protrude past the apertures 168 on the upper surface 86C of the manifold 86. Further rotation of the connector interface 84 may be stopped as the connector interface 84 abuts a surface (e.g., a ledge near the dimple 160) on the manifold which remains rotationally stationary.

While FIG. 12A illustrates that guide posts 166 that limit rotational twisting of the manifold 86 (and components of the connector assembly other than the connector interface 84), FIGS. 12B and 12C alternatively illustrate rotation stops 170 integrally formed with or otherwise attached to the manifold. The rotation stops 170 are received within corresponding grooves 172 of the outer cover 137. When the connector interface 84 is rotated (e.g., by twisting the finger grasp 138), the outer cover 137 is rotationally stationary with respect to the connector interface 84. Further, as a result of the coupling between the rotation stops 170 and the grooves 172 of the outer cover 137, the manifold 86 does not rotate, and remains rotationally stationary relative to the connector interface 84.

FIG. 17 illustrates the connector assembly 80 without the upper surfaces of the manifold 86, and the bellow housing 114 being illustrated with translucent shading. As seen therein, the connector assembly 80 comprises a pressure transducer housing 116 having a plurality of pressure sensors 701. The pressure transducer housing 116 can be coaxially aligned with the central axis of the catheter 2. The pressure transducer housing 116 may contact the bellow housing 114 so as to receive a pressure measurement from the catheter lumen 30 when the bellows 110 pressurize the catheter balloons 40. Accordingly, the pressure transducer housing 116 can have a plurality of pressure sensors 701, each corresponding to a bellow. FIG. 16 illustrates, for instance, two pressure sensors 701 located at the same radial and/or circumferential location as the bellows 110. The pressure transducer 7 may also have additional sensors, one or more memory and/or processor modules, communication modules, and electrical connections to connect to electrical connectors of the catheter 2. In some such examples, the integrated electrical connections and memory modules may permit determination of whether the catheter 2 has been previously used, and if so, the duration over which the catheter 2 was previously used. Further, such embodiments may also permit connecting to electrical elements in the catheter 2 to facilitate impedance or other biological measurements (such as ECG, EMG, pH) as described above. Advantageously, in such examples, connection of the catheter assembly as described herein can be an integrated fluid and electrical connection.

Embodiments of the present disclosure advantageously provide a multi-channel manometry system with simple connections to a catheter assembly. Such systems also advantageously permit simultaneously charging multiple balloons 40 by using a single charging mechanism, thereby eliminating complex connections between the catheter assembly and the charging mechanism. Further, the alignment and complementary connection of the catheter assembly with the connector assembly 80 may facilitate simultaneously fluidly and electrically connecting the catheter assembly with the connector assembly 80.

Various examples have been described. These and other examples are within the scope of this disclosure.

The invention claimed is:

1. A connector assembly for an anatomical manometry system, the anatomical manometry system comprising a catheter being generally elongate in shape and having a central axis, the catheter having a distal end and a proximal end, the distal end being configured for insertion into a patient lumen for measuring a pressure, the proximal end being opposite to the distal end, the catheter further including a plurality of catheter lumens permitting passage of a pressure transmission medium, the catheter further comprising a plurality of balloons on the distal end, each balloon being fluidly coupled to one of the plurality of catheter lumens so as to receive the pressure transmission medium, each balloon being configured to be inflatable and/or deflatable, the connector assembly comprising:

a connector interface that receives the proximal end of the catheter therethrough, the connector interface having an alignment element to permit alignment between the catheter and the connector interface;

a manifold having
 a plurality of first channels oriented in a direction parallel to the central axis, such that each first channel is aligned with a respective catheter lumen, when the catheter is connected to the connector interface and aligned therewith by the alignment element,
  a plurality of second channels, each second channel having a first opening and a second opening, the second opening of each second channel being fluidly coupled to a respective first channel, the first opening of each second channel being radially further outward of the central axis than the respective first channel, the manifold being connected with the connector interface; and
a charging mechanism connectable to the catheter via the connector interface, by a complementary connection, the charging mechanism comprising a plurality of chargers fluidly coupled to one or more of the plurality of first channels and one or more of the plurality of second channels of the manifold so as to permit passage of the pressure transmission medium from the charging mechanism toward the catheter lumen,
  each charger having a first end and a second end, the first end of each charger being connected to the first opening of a corresponding second channel,
  each charger having a fluid chamber and displacing a fluid in the fluid chamber, the chargers discharging the fluid to charge a corresponding balloon, whereby displacement of the fluid is caused by movement of each charger,
  the chargers being commonly actuable when the manifold is connected with the connector interface by the complementary connection, the commonly actuated chargers charging each balloon of the plurality of balloons.

2. The connector assembly of claim 1, wherein the plurality of chargers are commonly-housed on a charger housing, the charger housing being coaxial with the central axis of the catheter whereby each charger has a charger axis parallel to the central axis of the catheter.

3. The connector assembly of claim 2, wherein the first end of each charger contacts a first surface of the manifold, and the second end of each charger contacts the charger housing.

4. The connector assembly of claim 3, wherein the plurality of second channels are radial channels oriented in a radial direction, the radial channels being defined on a second surface of the manifold, the second surface being opposite to the first surface.

5. The connector assembly of claim 4, wherein each radial channel generally tapers along the radial direction.

6. The connector assembly of claim 2, further comprising a pressure transducer housing, the pressure transducer housing having a plurality of pressure sensors, the pressure transducer housing being coaxially aligned with the central axis of the catheter, the pressure transducer housing contacting the charger housing so as to receive a pressure measurement from the catheter lumen when the charger pressurize the balloons.

7. The connector assembly of claim 2, wherein the manifold and the charger housing are separated by a first axial distance when the catheter is disconnected from the connector interface, the manifold and the charger housing being separated by a second axial distance when the catheter is locked to the connector interface and/or charging has commenced, the second axial distance being less than the first axial distance.

8. The connector assembly of claim 1, wherein the plurality of first channels are defined at least partially within a body portion of the manifold.

9. The connector assembly of claim 1, wherein the first opening of each second channel has a first opening size and the second opening of each second channel has a second opening size, the first opening size being greater than the second opening size.

10. The connector assembly of claim 1, wherein the plurality of first channels are distributed symmetrically about the central axis.

11. A connector assembly for an anatomical manometry system, the anatomical manometry system comprising a catheter being generally elongate in shape, the catheter having a distal end and a proximal end, the distal end being configured for insertion into a patient lumen for measuring a pressure, the proximal end being opposite to the distal end, the catheter further including a plurality of catheter lumens permitting passage of a pressure transmission medium, the catheter further comprising a plurality of balloons on the distal end, each balloon being fluidly coupled to one of the plurality of catheter lumens so as to receive the pressure transmission medium, each balloon being configured to be inflatable and/or deflatable, the connector assembly comprising:
  a connector interface that receives the proximal end of the catheter therethrough;
  a manifold having a plurality of channels, each channel being aligned with a respective catheter lumen when the catheter is connected to the connector interface permitting passage of the pressure transmission medium toward the catheter lumen,
  the connector interface being rotatable relative to the proximal end of the catheter to lock the catheter to the manifold; and
  a charging mechanism coupled to the catheter and the connector assembly, the charging mechanism comprising a plurality of chargers commonly housed on a charger housing, each charger being fluidly coupled to plurality of channels of the manifold,
  the rotation of the connector interface relative to the manifold axially displacing the manifold relative to the charger housing so as to actuate each charger positioned on the charger housing, each charger displacing a fluid in the fluid chamber when actuated by the manifold,
  the chargers discharging the displaced fluid to charge a corresponding balloon, whereby displacement of the fluid is caused by movement of the charger when actuated by the manifold,
  the commonly actuated chargers further permitting charging each balloon of the plurality of balloons.

12. The connector assembly of claim 11, wherein the manifold further comprises a ramp portion defined near an outer perimeter thereof.

13. The connector assembly of claim 12, wherein the connector interface comprises a plurality of pins extending axially toward the manifold, wherein, the rotationally complementary connection comprises engagement of the plurality of pins with the ramp portion of the manifold.

14. The connector assembly of claim 13, wherein when the connector interface rotates relative to the manifold, each pin of the connector interface travels on the ramp portion of the manifold.

15. The connector assembly of claim 11, wherein the connector interface is rotatable between a first rotational position, a second rotational position, and a third rotational position, the first rotational position, the second rotational position and the third rotational position being spaced apart from each other along a circumferential direction.

16. The connector assembly of claim 15, wherein the first rotational position permitting insertion of the proximal end of the catheter through an aperture on the connector interface, the second rotational position corresponding to the proximal end of the catheter being locked relative to the connector interface so as to prevent removal of the proximal end from the connector interface.

17. The connector assembly of claim 11, wherein the chargers are arranged around a perimeter of the proximal end of the catheter when received within the connector interface.

18. An anatomical manometry catheter system, comprising:
   a catheter being generally elongate in shape and having a central axis,
      a distal end and a proximal end, the distal end being configured for insertion into a patient lumen for measuring a pressure, the proximal end being opposite to the distal end,
      a plurality of catheter lumens permitting passage of a pressure transmission medium,
      a plurality of balloons on the distal end, each balloon being fluidly coupled to one of the plurality of catheter lumens so as to receive the pressure transmission medium, each balloon being configured to be inflatable and/or deflatable;
   a connector assembly coaxially aligned with the catheter, the connector assembly being connectable to the proximal end of the catheter, the connector assembly having:
      a connector interface that receives the proximal end of the catheter, a manifold comprising a plurality of channels configured to deliver the pressure transmission medium therethrough toward a respective catheter lumen for inflating one or more balloons,
      the connector interface being rotatable relative proximal end of the catheter to lock the catheter to the manifold, and
      a charging mechanism fluidly coupled to the catheter, the charging mechanism comprising a plurality of chargers,
      whereby actuation of the plurality of chargers facilitates inflating each balloon of the plurality of balloons,
      each charger having a fluid chamber, the rotation of the connector interface relative to the manifold axially moving each charger of the plurality of chargers along the central axis and thereby displacing a fluid in the fluid chamber,
      the chargers discharging the fluid to charge a corresponding balloon, whereby rotation of the connector interface permits charging of each balloon of the plurality of balloons.

19. The anatomical manometry catheter system of claim 18, wherein the chargers include a plurality of bellows housed on a bellow housing, the bellow housing being coaxial with the central axis of the catheter whereby each bellow of the plurality of bellows has a bellow axis parallel to the central axis of the catheter, whereby the plurality of bellows are commonly actuable when the connector interface is connected to the catheter so as to simultaneously charge each balloon of the plurality of balloons.

20. The anatomical manometry catheter system of claim 18, wherein the plurality of chargers comprise a plurality of charging pistons, each charging piston being coupled to a respective catheter lumen and a respective channel of the plurality of channels, wherein each piston is commonly actuable by applying a force on an actuation handle to move each piston in a direction parallel to the central axis of the catheter, so as to transmit pressure transmitting medium in the respective channel toward the respective balloon and thereby charge the respective balloon.

21. The anatomical manometry catheter system of claim 18, wherein the catheter further comprises a central lumen positioned centrally about the central axis, the central lumen being generally surrounded by the plurality of catheter lumens, the central lumen being fluidly isolated from the plurality of catheter lumens.

22. The anatomical manometry catheter system of claim 21, wherein the central lumen is configured to deliver a liquid to the patient lumen.

23. The anatomical manometry catheter system of claim 18, wherein each balloon is positioned on an outer perimeter of the catheter, and wherein the catheter comprises a plurality of radial openings, each radial opening being positioned at a location corresponding to a respective balloon, the plurality of radial openings being configured to fluidly couple each balloon to a respective catheter lumen.

24. The anatomical manometry catheter system of claim 18, further comprising a plurality of pressure sensors, each of which is configured to receive a pressure measurement from a respective catheter lumen when the chargers pressurizes the balloons.

25. The anatomical manometry catheter system of claim 24, further comprising an electrical circuit electrically coupled to the plurality of pressure sensors and generating an electrical output corresponding to the measured pressure.

26. The anatomical manometry catheter system of claim 25, wherein the catheter comprises a plurality of electrical connectors configured to measure electrical impedance and/or other biological measurements, each of the plurality of electrical connectors of the catheter being operatively coupled to the electrical circuit.

27. The anatomical manometry catheter system of claim 26, wherein the catheter comprises
   one or more lumens extending longitudinally along the catheter, and
   one or more sensor wires, each sensor wire being positioned in a respective lumen, each sensor wire being connected to a corresponding electrical connector of the plurality of electrical connectors so as to permit measuring electrical impedance and/or other biological measurements.

28. The anatomical manometry catheter system of claim 25, further comprising at least one of a memory, a processor, and a communication circuits operatively coupled to the electrical circuit, at least one of the memory, processor and communication circuits configured to determine
   if the catheter connected to the anatomical manometry catheter system has been previously used, and if the catheter has been previously used, the duration over which the catheter was previously used.

* * * * *